US011268087B2

(12) United States Patent
Young

(10) Patent No.: US 11,268,087 B2
(45) Date of Patent: Mar. 8, 2022

(54) ISOLATION AND IMMOBILIZATION OF NUCLEIC ACIDS AND USES THEREOF

(71) Applicant: SIMPLSEQ, INC., Murrieta, CA (US)

(72) Inventor: Brandon Michael Young, Murrieta, CA (US)

(73) Assignee: SIMPLSEQ, INC., Murrieta, CA (US)

( * ) Notice: Subject to any disclaimer, the term of this patent is extended or adjusted under 35 U.S.C. 154(b) by 5 days.

(21) Appl. No.: 17/331,532

(22) Filed: May 26, 2021

(65) Prior Publication Data

US 2021/0371850 A1    Dec. 2, 2021

Related U.S. Application Data

(60) Provisional application No. 63/030,283, filed on May 26, 2020, provisional application No. 63/126,466, filed on Dec. 16, 2020.

(51) Int. Cl.
*C12N 15/10*    (2006.01)

(52) U.S. Cl.
CPC ..... *C12N 15/1065* (2013.01); *C12N 15/1006* (2013.01); *C12N 15/1096* (2013.01)

(58) Field of Classification Search
None
See application file for complete search history.

(56) References Cited

U.S. PATENT DOCUMENTS

2009/0215034 A1\* 8/2009 Maes et al. .......... C12Q 1/6827
435/6.13

OTHER PUBLICATIONS

Butt, Asif et al. "Overview of Circulating Nucleic Acids in Plasma/Serum: Update on Potential Prognostic and Diagnostic Value in Diseases Excluding Fetal Medicine and Oncology," Annals NY Academy of Sciences, vol. 1137, 236-42 (2008).

Casadio V. et al., "Urine cell-free DNA integrity as a marker for early prostate cancer diagnosis: a pilot study", Biomed Research International 2013: 270457 (2013).

Kemp BM et al., "How much DNA is lost? Measuring DNA loss of short-tandem-repeat length fragments targeted by the PowerPlex 16® system using the Qiagen MinElute Purification Kit," Hum. Biol. 86: 313-329 (2014).

Kosiova et al., "Synthesis of coumarin or ferrocene labeled nucleosides via Staudinger ligation," Beilstein J. Org. Chem. 2 2-5 (2006).

Motea et al., "Terminal deoxynucleotidyl transferase: The story of a misguided DNA polymerase," Biochimica et Biophysica Acta (BBA)—Proteins and Proteomics 1804: 1151-1166 (2010).

Mouliere, Florent et al. "High Fragmentation Characterizes Tumour-Derived Circulating DNA," PLOS One 6(9): e23418 (2011).

Mouliere, Florent et al., "Enhanced detection of circulating tumor DNA by fragment size analysis", Science Translational Medicine vol. 10 1-13 (2018).

Muthiah, Packianathan Thomas et al., "Crystal engineering of analogous and homologous organic compounds: hydrogen bonding patterns in trimethoprim hydrogen phthalate and trimethoprim hydrogen adipate", Beilstein J. Org. Chem. 2 1-8 (2006).

(Continued)

Primary Examiner — Kaijiang Zhang
(74) Attorney, Agent, or Firm — Perkins Coie LLP

(57) ABSTRACT

Disclosed is a novel technique of directly isolating nucleic acids from a biological sample and use of the isolated nucleic acid complexes for various applications and assays such as biobanking and sequencing.

29 Claims, 36 Drawing Sheets
Specification includes a Sequence Listing.

Spin Blood Sample

Separate Plasma

Bind to Streptavidin Beads

Single Stranded Tailed DNA Bound to Streptavidin Beads

Biotin Tailed cfDNA

(56) References Cited

OTHER PUBLICATIONS

Rashid, "The strategies of DNA immobilization and hybridization detection mechanism in the construction of electrochemical DNA sensor: a review," Sensing and Bio-Sensing Research 16: 19-31 (2017).
Sasaki R. et al., "TdT activity in bone-marrow serum in patients with leukemia," The New England J. of Medicine 304: 1108 (1981).
Moritz et al., "Simple methods for the 3' biotinylation of RNA", RNA Mar. 2014 vol. 20, No. 3, pp. 421-427.
USPTO/ISA, Invitation to Pay Additional Fees for PCT/US21/34344, Sep. 7, 2021.

* cited by examiner

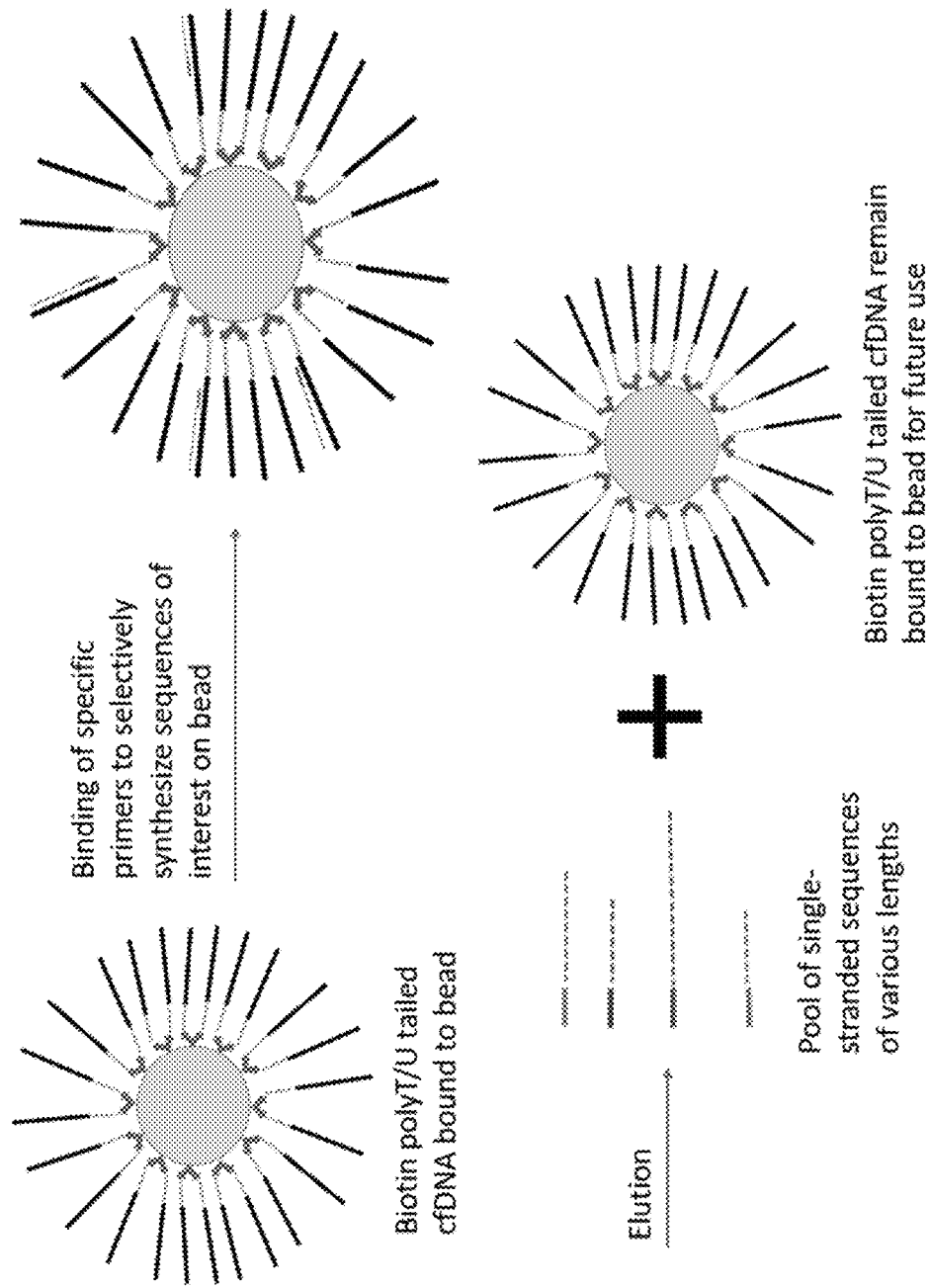

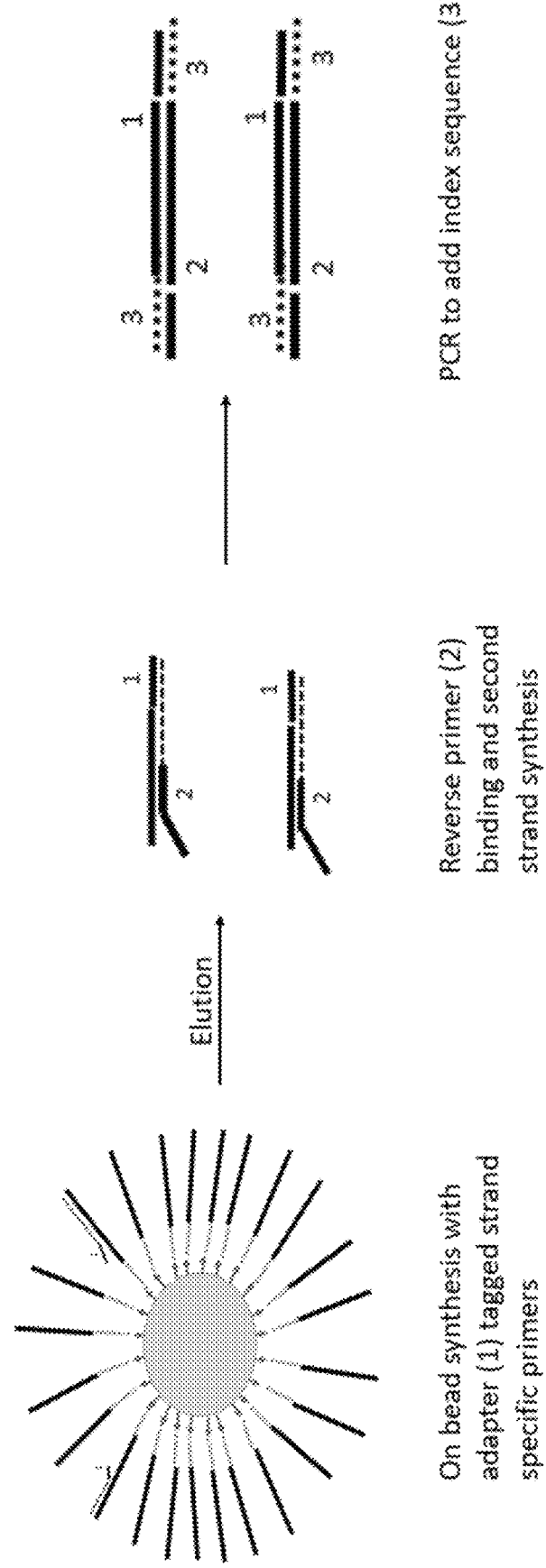

Figure 13

MTHFR rs1081133 C Allele   GCTGACCTGAAGCACTTGAAGGAGAAGGTGTCTGCGGGAGCCGATTTCATCATCACGCGCAGCTTTCTTTGAGGCTGACACATTCTTCCGCTTTGTGAAGGCATGCACCGACAT MTHFR rs1081133 T Allele   GCTGACCTGAAGCACTTGAAGGAGAAGGTGTCTGCGGGAGTCGATTTCATCATCACGCGCAGCTTTCTTTGAGGCTGACACATTCTTCCGCTTTGTGAAGGCATGCACCGACAT MTHFR rs1081133 RC         ATGTCGGTGCATGCCTTCCCGCAGACACCTTCTCCTTCAAGTGCTTCAAGGTCAGCCTGATGATGAAATCGCTCCCGCAGAGCTGCGTGATGATGAAGAAAAGCGGAAGAAGCG

SEQUENCE LISTING

```
<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: tail

<400> SEQUENCE: 1
tttttttttu tttttttutt ttuttttut                                29

<210> SEQ ID NO 2
<211> LENGTH: 28
<212> TYPE: DNA
<213> ORGANISM: Artificial Sequence
<220> FEATURE:
<223> OTHER INFORMATION: tail

<400> SEQUENCE: 2
tttttttttu tttttttutt ttuttttt                                 28

<210> SEQ ID NO 3
<211> LENGTH: 10
<212> TYPE: DNA
<213> ORGANISM: Artificial Sequence
<220> FEATURE:
<223> OTHER INFORMATION: primer

<400> SEQUENCE: 3
tttttttttu                                                     10

<210> SEQ ID NO 4
<211> LENGTH: 113
<212> TYPE: DNA
<213> ORGANISM: Homo sapiens

<400> SEQUENCE: 4
gctgacctga agcacttgaa ggagaaggtg tctgcgggag ccgatttcat catcacgcag    60
cttttctttg aggctgacac attcttccgc tttgtgaagg catgcaccga cat          113

<210> SEQ ID NO 5
<211> LENGTH: 113
<212> TYPE: DNA
<213> ORGANISM: Homo sapiens

<400> SEQUENCE: 5
gctgacctga agcacttgaa ggagaaggtg tctgcgggag tcgatttcat catcacgcag    60
cttttctttg aggctgacac attcttccgc tttgtgaagg catgcaccga cat          113
```

```
<210> SEQ ID NO 6
<211> LENGTH: 113
<212> TYPE: DNA
<213> ORGANISM: Homo sapiens

<400> SEQUENCE: 6
atgtcggtgc atgccttcac aaagcggaag aatgtgtcag cctcaaagaa aagctgcgtg      60
atgatgaaat cggctcccgc agacaccttc tccttcaagt gcttcaggtc agc            113

<210> SEQ ID NO 7
<211> LENGTH: 10
<212> TYPE: DNA
<213> ORGANISM: Artificial Sequence
<220> FEATURE:
<223> OTHER INFORMATION: primer

<400> SEQUENCE: 7
aaaaaaaaaa                                                             10

<210> SEQ ID NO 8
<211> LENGTH: 12
<212> TYPE: DNA
<213> ORGANISM: Artificial Sequence
<220> FEATURE:
<223> OTHER INFORMATION: primer

<400> SEQUENCE: 8
tttttttttt tt                                                          12
```

US 11,268,087 B2

ISOLATION AND IMMOBILIZATION OF NUCLEIC ACIDS AND USES THEREOF

PRIORITY CLAIM

This application claims priority to U.S. Provisional Patent Application No. 63/030,283, filed May 26, 2020, and U.S. Provisional Patent Application No. 63/126,466, filed Dec. 16, 2020, the contents of which are hereby incorporated by reference in their entireties.

SEQUENCE LISTING

This application contains a Sequence Listing, which was submitted in ASCII format via EFS-Web and is hereby incorporated by reference in its entirety. The ASCII copy, created on May 26, 2021, is named SimplSeq Sequence Listing 137682-8001.US02_ST25.txt and is 2 KB in size.

BACKGROUND

The completion of the human genome project revealed that cancer and many other diseases have a substantial genetic component. Because of this, the ability to accurately and efficiently sequence an individual's genome, or portions of the genome with diagnostic or clinical significance for a particular disease, has become increasingly important. In addition to analyzing patients' genomes, analyzing their transcriptomes can be useful in quantifying the expression of genes with diagnostic or clinical significance. Therefore, there is a need of improving the technology of processing massive nucleic acid samples and generating nucleic acid pools. This disclosure provides a novel approach to satisfy the needs.

SUMMARY

In one aspect, this disclosure relates to a method of directly isolating a nucleic acid from a biological sample. The method entails the steps of contacting a biological sample containing a nucleic acid directly with a reaction mix to obtain a tagged nucleic acid; and contacting the tagged nucleic acid with a solid support such that the tagged nucleic acid binds to a surface of the solid support; and washing the solid support thereby to obtain isolated nucleic acid bound to the surface of the solid support. In certain embodiments, the nucleic acid is DNA or RNA. In certain embodiments, the nucleic acid is double stranded or single stranded. In certain embodiments, the double stranded nucleic acid is denatured to single stranded nucleic acid before or after contacting the biological sample with the reaction mix. In certain embodiments, the reaction mix comprises a template-independent DNA or RNA polymerase, and one or more NTPs, dNTPs or ddNTPs, wherein at least a fraction of the one or more NTPs, dNTPs or ddNTPs are modified by an affinity tag, and wherein the unmodified and modified NTPs, dNTPs or ddNTPs form a polymeric tail incorporating the affinity tag. In certain embodiments, the reaction mix comprises terminal transferase (TdT), dTTP and dUTP, and wherein dUTP is biotinylated to form a polymeric tail incorporated with biotin. In certain embodiments, the isolated nucleic acid bound to the surface of the solid support is removed from the solid support by enzyme digestion. In certain embodiments, the reaction mix comprises terminal transferase (TdT), dUTP and ddUTP, and wherein dUTP or ddUTP is biotinylated to form a polymeric tail incorporated with biotin. In certain embodiments, the surface of the solid support is coated with one or more chemical groups which are binding partners of the affinity tag. In certain embodiments, the surface of the solid support is coated with avidin, streptavidin, or neutravidin. In certain embodiments, the polymeric tail is attached to the 3' end of the nucleic acid. In certain embodiments, the biological sample comprises blood, plasma, serum, urine, saliva, exosomes, a lysed formalin-fixed, paraffin-embedded (FFPE) tissue sample, a sample containing extracted or purified nucleic acid, and cells. In certain embodiments, the solid support is a bead, a plate, or a column.

In another aspect, disclosed is a method of generating a cDNA library from a biological sample. The method entails the steps of obtaining an isolated nucleic acid bound to a solid support as disclosed above, hybridizing one or more primers to the isolated nucleic acid; conducting primer extension using the isolated nucleic acid as template to synthesize cDNA fragments; and eluting the synthesized cDNA fragments from the solid support. In certain embodiments, the primer is a sense strand primer or an anti-sense strand primer. In certain embodiments, the primer is a specific primer. In certain embodiments, the primer is a random primer. In certain embodiments, the one or more primers bind to different nucleic acid fragments. In certain embodiments, the one or more primers bind to different locations of the same nucleic acid fragment. In certain embodiments, the one or more primers bind to the same location of different nucleic acid fragments. In certain embodiments, the method further entails annealing the eluted sense strand cDNA fragments and anti-sense strand cDNA fragments; and extending the annealed cDNA fragments to fill in the gap thereby to obtain double stranded cDNA fragments.

In another aspect, disclosed is a captured nucleic acid complex obtained by the method disclosed herein. The captured nucleic acid complex comprises a solid support, and a plurality of nucleic acid fragments directly isolated from a biological sample, each fragment having a 3' end bound to a polymeric tail, and each polymeric tail is bound to a partner molecule attached to a solid support. In certain embodiments, the solid support is a bead, a plate, or a column. In certain embodiments, the nucleic acid is DNA or RNA. In certain embodiments, the nucleic acid is single-stranded. In certain embodiments, the nucleic acid is double-stranded. In certain embodiments, the polymeric tail comprises a priming location to bind a universal primer for copying or amplifying the nucleic acid fragment. In certain embodiments, the nucleic acid fragment comprises a priming location to bind a specific primer for copying or amplifying the nucleic acid fragment. In certain embodiments, a part of the nucleic acid fragment is copied or amplified. In certain embodiments, the entire nucleic acid fragment is copied or amplified.

In another aspect, disclosed herein is a biobank comprising a plurality of complexes disclosed herein, each complex comprising a plurality of nucleic acid fragments present in a biological sample. In certain embodiments, the plurality of the complexes comprises substantially all nucleic acid fragments present in the biological sample. In certain embodiments, the plurality of the complexes comprises only the target nucleic acid fragments of interest present in the biological sample. In certain embodiments, the nucleic acid fragment comprises a genomic DNA fragment.

BRIEF DESCRIPTION OF THE DRAWINGS

FIG. 4A illustrates the use of isolated nucleic acids for assays with specific primers to obtain a pool of single-stranded sequences of interest. FIG. 4B illustrates that the specific primers can be tagged for on-bead cDNA synthesis, and then reverse primers and index sequences can be used to obtain a library containing indexed sequences of interest. (SEQ ID NO: 3.)

FIG. 5A shows that primers bind to sense and antisense strands of DNA/RNA bound to a solid support. FIG. 5B shows cDNA synthesis from the sense and antisense strands. FIG. 5C shows that cDNA of varying lengths is eluted while the input sense and anti-sense strands remain bound to the solid support. FIG. 5D shows that the sense and antisense cDNA strands are annealed.

FIG. 13 shows the sequences of the DNA samples used for testing. (SEQ ID NOs: 4-6.)

FIG. 14A: Lanes 1-4 show DNA with 8-hour, 4-hour, 2-hour, 1-hour reaction time, respectively, and Lane 5 shows DNA with no TdT added. FIG. 14B: Lanes 1-2 show MTHFR oligonucleotide duplex with C allele and T allele, respectively, at rs180133, and Lanes 3-4 show MTHFR oligonucleotide duplex with C allele and T allele, respectively, at rs180133, poly T/U biotin tailed.

FIG. 20A shows appropriately mixed base content of random hexamer followed by 100% PolyA preceding genomic DNA data for Read 1.

FIG. 24A illustrates that 3' tailed DNA or RNA (1) is bound to a solid support. cDNA is synthesized from a specific primer (2) attached to a stubby adapter (3). The adapters (4) are ligated to the cDNA on bead and the specific primed cDNA is eluted and amplified by PCR primers (5) to create a library. FIG. 24B illustrates that 3' tailed DNA or RNA (1) is bound to a solid support. cDNA is synthesized from a polyA primer (2) attached to a stubby adapter (3). The adapters (4) are ligated to the cDNA on bead and the polyA primed cDNA is eluted and amplified by PCR primers (5) to create a library.

FIG. 27A shows that RNA bound to a solid support is used as the staring input material for reverse transcription of the first strand cDNA synthesis. FIG. 27B shows that after elution, the input RNA remains bound to the solid support, while the eluted polyA primed first strand cDNA serves as templates for the second strand cDNA synthesis with specific primers or random hexamer primers, which primers are optionally tagged with stubby adapters such as i5 and i7 stubby adapters. FIG. 27C shows that the double-stranded cDNA product of the second strand cDNA synthesis include specific double stranded cDNA products and random primed double-stranded cDNA products having variable lengths. These cDNA products can then serve as the input to a PCR reaction that adds adapter indexing barcode sequences for use on Illumina NGS instrumentation. (SEQ ID NO: 3.)

DETAILED DESCRIPTION

Figure 1:
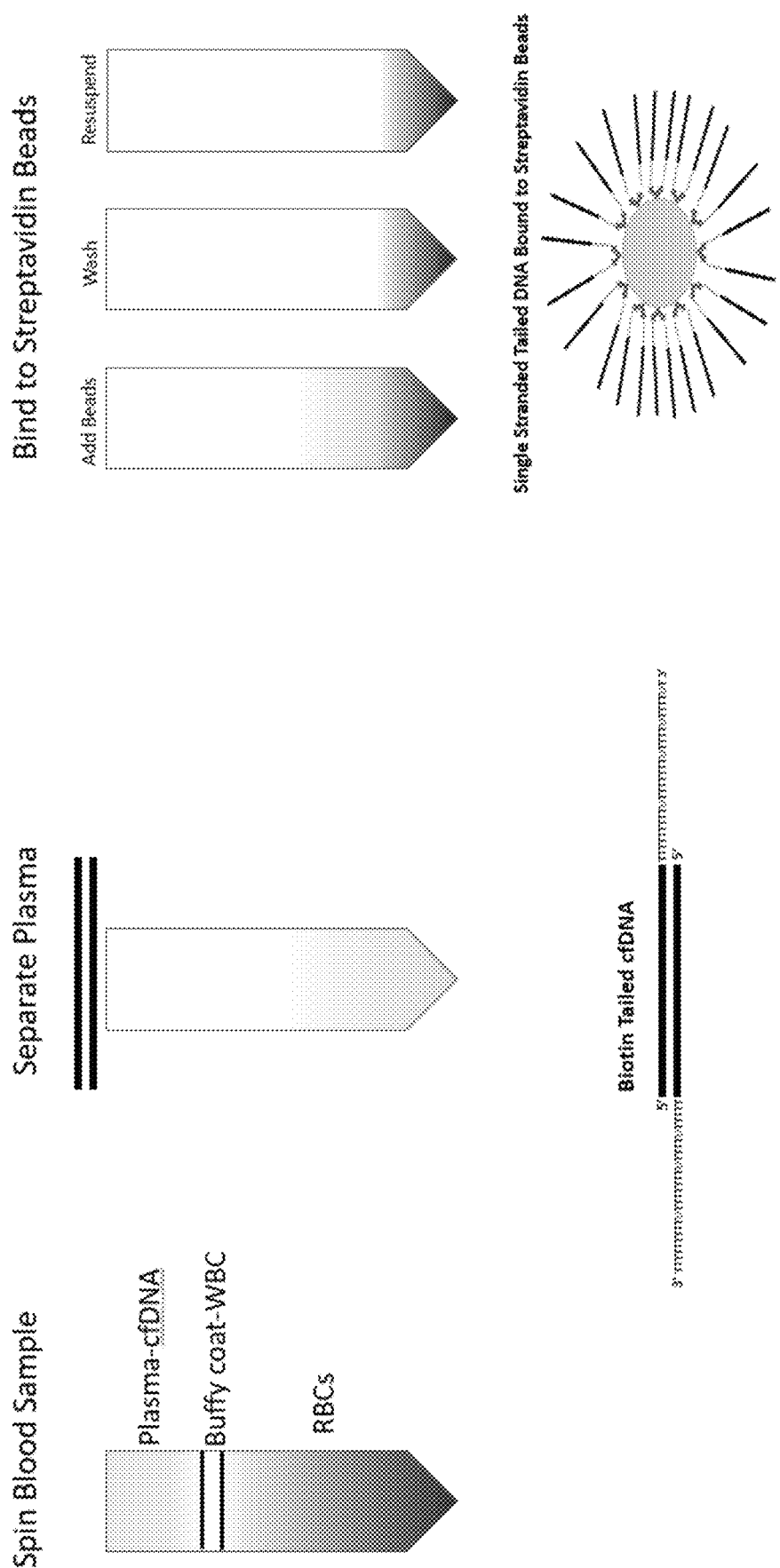
FIG. 1 illustrates direct isolation of circulating free DNA (cfDNA) from a blood sample using a biotin tag and streptavidin-coated beads. This diagram is used for illustrative purposes only but not limited to a blood sample or cfDNA. All types of nucleic acids can be extracted by this procedure. The same process can be used for all biological samples. The blood sample is spun to separate the blood components into three layers: the top layer is plasma containing cfDNA, the middle layer is buffy coat containing white blood cells, and the bottom layer contains the red blood cells. The cfDNA may be single-stranded or double-stranded. Most cfDNA has a size of less than 200 bp. Next, the plasma containing cfDNA is separated and mixed directly without purification with a reaction mix containing a suitable buffer, a terminal transferase, dTTP, and dUTP-biotin at room temperature to produce biotin-tailed cfDNA. The streptavidin coated beads are added such that the biotin-tailed cfDNA are bound to the surface of the streptavidin beads. (SEQ ID NOs: 1-2.)

Direct Isolation of Nucleic Acids from Samples

In one aspect, this disclosure relates to a method of directly isolating nucleic acids from a biological sample such as blood, serum, plasma, saliva, exosomes, a lysed formalin-fixed, paraffin-embedded (FFPE) tissue sample and cells or any sample containing extracted or purified nucleic acids. The nucleic acids can be DNA or RNA, and can be double-stranded or single-stranded. In some embodiments, the DNA and RNA are co-purified if both are present in the biological sample. The method entails contacting the biological sample with a reaction mix containing one or more NTPs, dNTPs or ddNTPs, at least a fraction of which is modified with an affinity tag or a binding moiety, and an enzyme such that a polymeric tail comprising the one or more NTPs, dNTPs or ddNTPs is added to the 3' end of the nucleic acids, contacting the biological sample containing the tailed nucleic acids with a solid support such that the tailed nucleic acids bind to the surface of the solid support via affinity or covalent binding between the tail and the surface of the solid support, and removing the unbound nucleic acids from the reaction mix thereby to obtain isolated nucleic acids bound to the surface of the solid support. In some embodiments, the biological sample is treated with a detergent such that the cfDNA is released from the exosomes. Alternatively, the exosomes are isolated from the biological samples and then subjected to detergent treatment such that the cfDNA from the exosomes are separately analyzed.

The disclosed technology can be used for isolating and purifying nucleic acids from multiple sample types. In one embodiment, the nucleic acids can be isolated from a biological sample without the use of protease or chemicals that affect proteins and metabolites. This allows for downstream proteomics and metabolomics to be performed on the bead binding supernatant. In another embodiment, a protease can be used to digest the proteins that are bound to the nucleic acid molecules. The protease can be thermolabile (www.giagen.com/us/products/discovery-and-translational-research/lab-essentials/enzymes/giagen-protease-and-proteinase-k/?clear=true). In some embodiments, a commercially available protease inhibitor (www.thermofisher.com/order/catalog/product/A32963#/A32963) can be added after digestion allowing enzymatic tailing reaction. Proteases useful for the disclosed technology include, but are not limited to, heat labile proteases, proteinase K, and, Glu-c.

In various embodiments, the enzyme is a template-independent DNA or RNA polymerase which adds a polymeric tail to the 3' end of a nucleic acid by incorporating modified and/or unmodified NTPs, dNTPs or ddNTPs. The enzymes include but are not limited to terminal transferase, polyA polymerase, polyU polymerase, E. Coli DNA polymerase, Klenow Fragment, T4 DNA polymerase, T7 DNA polymerase, phi29 DNA polymerase, BST DNA polymerase, and BSU DNA polymerase. In some embodiments, the one or more NTPs, dNTPs or ddNTPs include natural and synthetic NTPs, dNTPs or ddNTPs. In some embodiments, dNTPs such as dATP, dTTP and dUTP are preferred. In some embodiments, ddNTPs such as ddATP, ddTTP and ddUTP are preferred.

In certain embodiments, the nucleic acid includes circulating nucleic acids in serum or plasma such as circulating free DNA (cfDNA). Circulating nucleic acids have proven to be a powerful tool in the diagnostic industry ranging from non-invasive prenatal testing to cancer[1]. The cfDNA is often found degraded to sizes ranging from about 70 base pairs and about 200 base pairs. The cfDNA includes single-stranded and double-stranded DNA fragments. Used in disease diagnosis, especially cancer, cfDNA is of particular interest because DNA mutations are known to be a causative driver of the disease which predicts progression and responds to therapy[2]. The disclosed techniques can isolate cfDNA or other nucleic acids of any sizes and can be applied to other nucleic acids such as DNA and RNA from other sources or biological samples.

Current extraction methods using beads and columns rely on electric charge to bind nucleic acids but lead to non-specific binding of nucleic acids, proteins and other molecules. There is no guarantee that all of the nucleic acids, especially nucleic acids of different lengths will bind and remain bound when competing with other charged molecules. Wash steps with buffers and alcohol are required to remove the contaminating biological samples but may result in removal of the bound nucleic acids of interest. Experiments using beads and columns with purified nucleic acids such as DNA as a control showed a loss of 20%-60%, with a mean loss of 39%[3].

The novel technique disclosed herein uses enzymatic reactions which can work directly in a biological sample such as blood, plasma or serum to attach a polymeric tail to the 3' end of the nucleic acids present in the biological sample, which polymeric tail specifically binds to the surface of a solid support and is used for isolating and purifying the nucleic acids. The disclosed technology entails binding DNA and RNA molecules based on the specific affinity tail added in the first step of the reaction process. This step can be performed in various biological samples such as blood, plasma, serum, urine, saliva, sputum, tissue, bone, lysed FFPE, cells, exosomes, and biological samples of non-human or non-animal origin. Although the technique disclosed herein can be performed on nucleic acids that have already been extracted or purified, prior extraction or purification using a conventional technique such as column or bead purification or gel purification is not required for tagging the nucleic acids of interest. In some embodiments, the reaction mix contains dNTPs, ddNTPs, or both. One or more NTPs, dNTPs or ddNTPs, or at least a fraction of NTPs, dNTPs or ddNTPs, are modified by adding an affinity tag (such as biotin) or a binding moiety, which modification allows specific binding to the binding partner coated on the surface of a solid support. In one example, dUTP is modified with an affinity tag while dTTP is unmodified in a reaction mix. In another example, only dTTP is used in a reaction mix while less than 100% of the dTTP is modified with an affinity tag. Using dNTPs with modification requires a more precise ratio to assure that each tail has a modified base. Some polymeric tails may have multiple modified dNTPs and a longer size to ensure that a sufficient amount of modified dNTPs was incorporated. With ddNTPs the tail is terminated once it is added to the nucleic acid molecules to allow more precise calculation of the amount of ddNTP needed based on the number of the nucleic acid molecules or the amount of 3' ends. In one example, the reaction mix comprises unmodified dTTP and biotinylated dUTP. In another example, the reaction mix comprises unmodified dTTP and dUTP along with modified dUTP, ddCTP and ddUTP. In another example, the reaction mix comprises unmodified dUTP along with modified dUTP, ddCTP and ddUTP. As one skilled in the art would understand, various combinations of modifications can be applied to the disclosed technology including modification of one or more types of NTPs, dNTPs or ddNTPs, or modifications with different affinity tags. For example, the reaction mix may comprise only one type of dNTP or ddNTP (e.g., dUTP) which is modified. Alternatively, the reaction mix may comprise two or more types of dNTPs or ddNTPs (e.g., dUTP, ddCTP, and ddUTP) are modified. In yet another example, the reaction mix may comprise a combination of biotinylated dUTP and ddUTP modified by click chemistry. The reaction mix can be added directly to a biological sample containing the nucleic acids of interest. It is not required that the nucleic acids of interest are extracted, isolated, or purified from the biological sample prior to adding the reaction mix.

Figure 26:
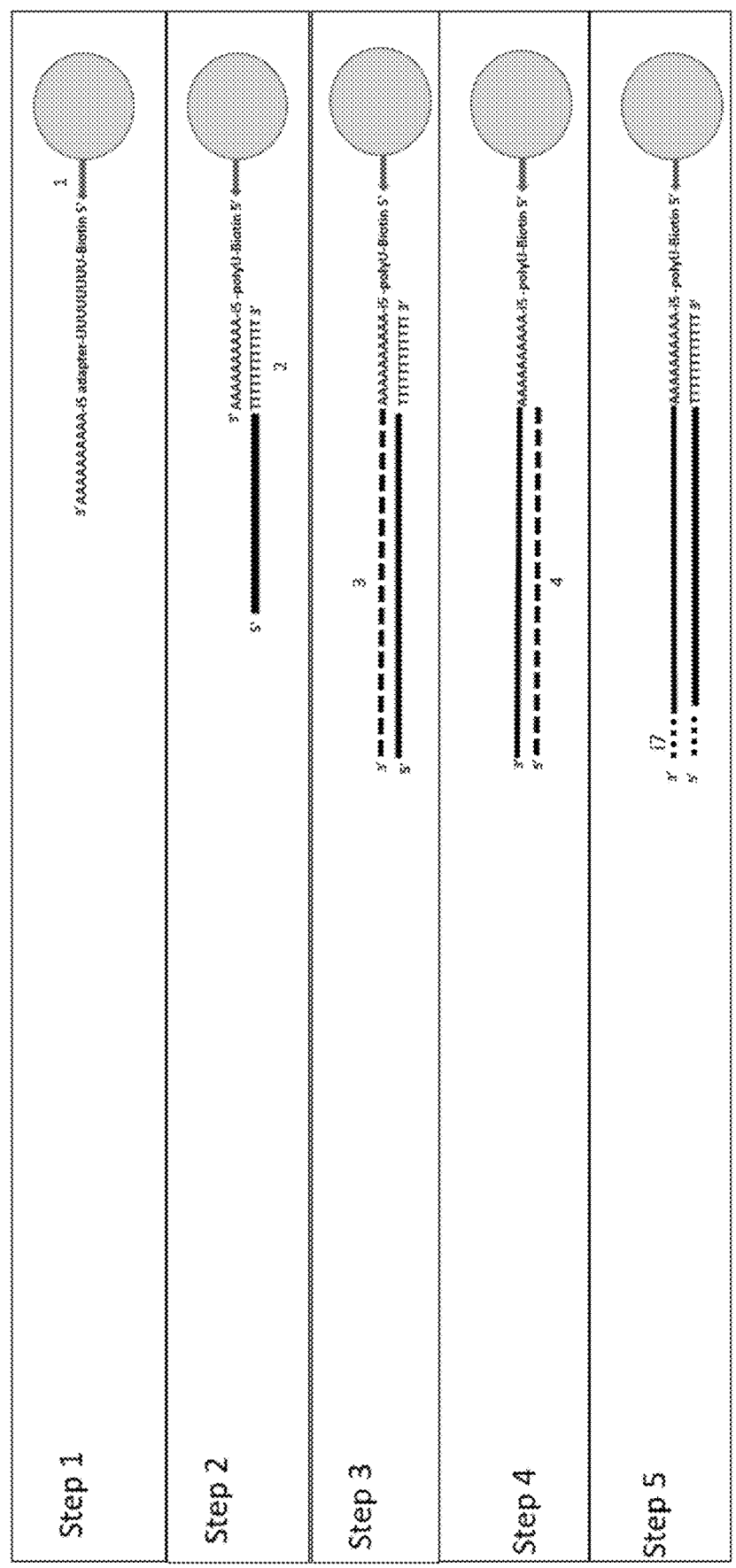
FIG. 26 illustrates a process of bound polyA RT cDNA synthesis. In step 1, the 5' end of the polyA oligo is attached to a solid support via i5 adapter biotin-polyU tail. In step 2, the input RNA is hybridized to polyA. In step 3, the cDNA is synthesized, and the input RNA is degraded by RNase H digestion. In step 4, the second strand is synthesized from a random hexamer primer or a specific primer. In step 5, PCR amplification is performed on bead using the i5 and i7 primers. Only the bound molecule having i5 and i7 primers can be amplified. (SEQ ID NOs: 7-8.)

In some embodiments, the NTPs, dNTPs, or ddNTPs are not modified when being incorporated into a polymeric tail. As illustrated in FIG. 26, bound oligo dT can be used to prime polyA tailed nucleic acid and to perform cDNA synthesis without using a polymeric tail incorporating affinity tags. cDNA synthesis on oligo dT beads are commercially available (e.g., www.neb.com/protocols/0001/01/01/cdna-synthesis-on-oligo-dt25-magnetic-beads-s1419).

In some embodiments, the enzyme is terminal transferase (TdT), which is a template-independent polymerase that catalyzes the addition of dNTPs or ddNTPs or modified dNTPs or ddNTPs to the 3' end of protruding, recessed, or blunted-ended single-stranded or double-stranded DNA[4]. The modified NTPs, dNTPs or ddNTPs can be incorporated in this nascent strand providing the binding moiety or affinity tag. For example, certain dNTPs or ddNTPs may be biotinylated. Other DNA or RNA polymerases can be used for attaching an affinity tag to the nucleic acids as well. DNA dependent DNA polymerases, DNA dependent RNA polymerases, RNA dependent DNA polymerases and RNA dependent RNA polymerases may be used. These include but are not limited to: terminal Transferase, Klenow Fragment, *E. Coli* Poly (A) polymerase. This type of binding will be specific for the affinity tag and also orient the nucleic acid molecule in a manner that allows unobstructed reverse complement polymerization to complete at the 5' end of the molecule with steric hinderance that would occur if the molecule was bound at the 5'.

3' extension of nucleic acids results in polymeric tails attached to the nucleic acids, allowing isolation of the nucleic acids directly from the sample. It has been shown previously that TdT is active in serums. In some embodiments, the polymeric tail comprises one or more NTPs, dNTPs or ddNTPs, at least a fraction of which are modified with an affinity tag. In some embodiments, the ratio of unmodified NTPs, dNTP or ddNTP:modified NTPs, dNTP or ddNTP is 95:5. For example, the polymeric tail comprises unmodified dTTP and dUTP modified with an affinity tag such as biotin. When the biological sample is in contact with a reaction mix comprising TdT, dTTP, and biotinylated dUTP, the nucleic acids in the biological sample are attached with a biotin tail comprising dTTP and dUTP-biotin such that upon subsequent contact with a solid support which surface is coated with avidin, streptavidin, or neutravidin, the biotin tailed nucleic acids are bound to the surface of the solid support via highly specific affinity binding. Depending on the reaction time, the polymeric tail can have various lengths. Also, the ratios of unmodified NTP, dNTP or ddNTP:modified dNTP or ddNTP can be adjusted to include a wide range. For example, the amount of unmodified NTPs, dNTPs or ddNTPs in the reaction mix can be from 0-99.9%, while the modified NTPs, dNTP or ddNTPs can be 100%-0.1%. Ratios of unmodified:modified NTP, dNTP or ddNTP can be varied based on the length of tail produced on the nucleic acid molecule, with the high ratios used for shorter tails to ensure that a modified NTP, dNTP or ddNTP is incorporated into the tail. The length of the tail can be optimized based on various factors such as the reaction and the nucleic acids of interest.

Biotin-avidin affinity binding is one of the strongest non-covalent bonds. Other functional binding mechanisms such as covalent bonding can be used, including but not limited to amine EDC, and click chemistry. As used herein, "affinity tag" include but are not limited to tags attached to nucleic acids via affinity binding or covalent reactive modifications to the NTPs, dNTPs or ddNTPs. In certain embodiments, affinity tags include but are not limited to the following commercially available products: aminoallyl-dNTPs/ddNTPs, biotin-AA-dNTPs/ddNTPs, 2-amino-dATP/ddATP, 7-deaza-dGTP, 7-deaza-dATP, 5-methyl-dCTP, 5-iodo-dUTP, 5-bromo-dUTP, 5-fluoro-dUTP, N4-methyl-dCTP, 5-propynyl-dUTP and 5-propynyl-dCTP, 2-thio-dTTP, 4-thio-dTTP and alpha-thio-dNTPs, 5-ethynyl-2'-deoxyuridine, biotin-16-ddUTP, biotin-11-ddCTP, 5-DBCO-PEG4-dCTP, 3'azido-2',3'-ddUTP, azide-PEG4-aminoallyl-dUTP. Covalent binding can be used when long term storage of the isolated nucleic acids is anticipated. Various techniques are known in the art[6]. In some embodiments, azide-modified dUTPs are used in a chemical reaction approach to allow primary amines to covalently bind to a solid support. Azides are used because of their temperature stability and because they do not naturally occur in biological samples such as proteins and nucleic acids. This reduces cross-reactivity of biological samples containing amine groups with charge-based binding moieties such as those used with aminoallyl-dUTP.

In certain embodiments, the binding is based on copper-free click chemistry. The reaction involves the use of a diarylcyclooctyne moiety (DBCO) with an azide-modified reaction partner, known as strain-promoted alkyne azide cycloaddition (SPAAC). Unlike standard click chemistry, this reaction is fast at room temperature and does not require a cytotoxic Cu(I) catalyst. The strain-promoted or Cu(I)-free cycloaddition (SPAAC) strategy relies on the use of strained cyclooctynes. Diarylcyclooctynes are thermally stable compounds with very narrow and specific reactivity toward azides. Their use decreases the activation energy for the cycloaddition click reaction, allowing it to be carried out without the need for catalysis at low temperatures with an efficiency greater than that of the Cu(I)-catalyzed ligation.

Figure 2:
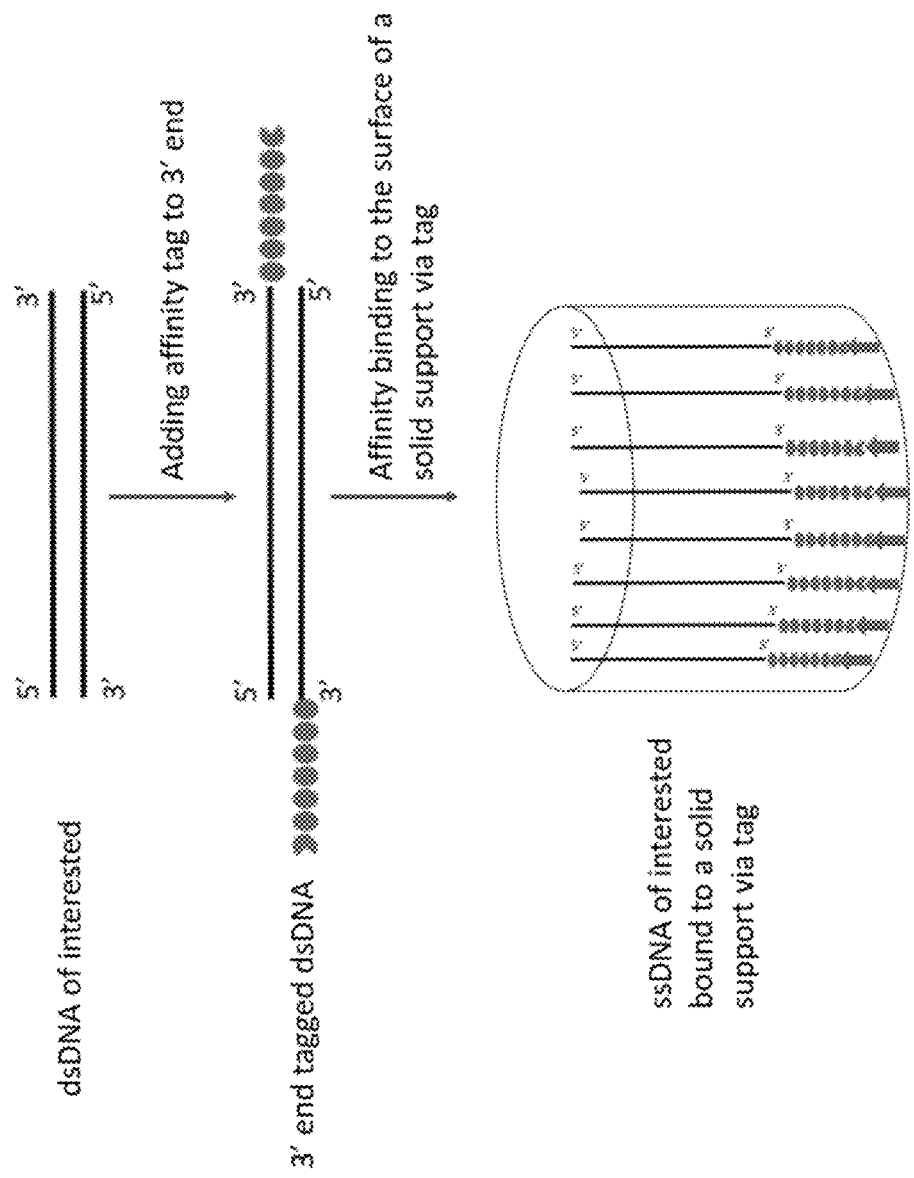
FIG. 2 illustrates attaching affinity tags to the 3' end of DNA and binding the tagged DNA to the surface of a well in a plate. The dsDNA can be denatured to obtain ssDNA before or after adding the affinity tags.

FIG. 2 illustrates the process of attaching an affinity tag to a nucleic acid fragment in a sample and binding the tagged nucleic acid fragment to a surface of a solid support, which surface is coated with a corresponding binding partner of the affinity tag. One or more NTPs, dNTPs or ddNTPs can be modified by an affinity tag and a polymeric tail is synthesized incorporating the one or more modified NTPs, dNTPs or ddNTPs. The polymeric tail is attached to the 3' end of the nucleic acid fragment. Various affinity tags and their binding partners can be used in the disclosed technology. In some embodiments, the affinity tag and/or the binding partner are not naturally occurring in cells such that the binding reaction is specific between the tagged nucleic acid fragments and the solid surface coated with the binding partner of the affinity tag.

Non-limiting examples of affinity tags and binding partners include: (1) amine ($-NH_2$) modified dNTPs binding on the surface of the solid support coated with any one or more of the following chemical groups: NHS ester, imidoester, pentaflourophenyl ester, or hydroxymethyl phosphine; (2) carboxyl ($-COOH$) modified dNTPs binding on the surface of the solid support coated with a carbodiimide such as 1-ethyl-3-(3-dimethylaminopropyl) carbodiimide (EDC); (3) sulfhydryl ($-SH$) modified dNTPs binding on the surface of the solid support coated with any one or more of the following chemical groups: maleimide, haloacetyl (bromo or iodo), pyridyldisulfide, thiosulfonate, or vinylsulfonate; (4) aldehyde ($-CHO$) modified dNTPs binding on the surface of the solid support coated with any one or more of the following chemical groups: hydrazide or alkoxyamine; and (5) azide ($-N3$) modified dNTPs binding on the surface of the solid support coated with phosphine. In this embodiment, the Staudinger ligation occurring between an azide ($-N3$) and a methyl ester phosphine ($-P3$) is of particular interest because these chemical groups do not naturally occur in cells such that they have specificity to each other without the possible cross-reactivity from biological samples[7].

The tailed or untailed nucleic acid molecules can be treated with slightly basic conditions, such as addition of NaOH to a final concentration of 0.02 N, or by heating to a high temperature such as 95° C., to separate the hybridized strands thereby to obtain single-stranded nucleic acid.

The nucleic acids bound to the solid support can be removed by enzyme digestion. For example, certain enzymes that specifically digest dUTP (e.g., uracil-specific excision reagent (USER) enzyme or thermolabile USER II enzyme from NEB) can be used to remove the bound nucleic acids from the solid support.

Use of the Isolated Nucleic Acids in Various Assays

In another aspect, the nucleic acids obtained by the method disclosed herein have various uses in various assays, for example, generating a gene pool, a biobank or biorepository, or a cDNA library. In some embodiments, a gene pool, a biobank or a biorepository for immediate or future use can be generated by one or more captured nucleic acid complexes as detailed in the section below. Using a collection of the isolated single-stranded nucleic acids bound to a solid support as templates, various reactions such as PCR (e.g., qPCR, and ddPCR), primer extension, Sanger or Next Generation sequencing can be performed directly on the solid support. The use of solid support for immobilizing nucleic acids is known in the art. For example, multi-well plates or microarrays can be used as a solid support, where tagged nucleic acids are bound to the surface of each well such that one or more plates or microarrays have a pool of gene of interest. In another example, beads or columns can be used as solid support, where the surface of each bead or column is bound with tagged nucleic acids such that an entire pool of nucleic acids of interest can be loaded to one or more beads or columns.

Figure 3:
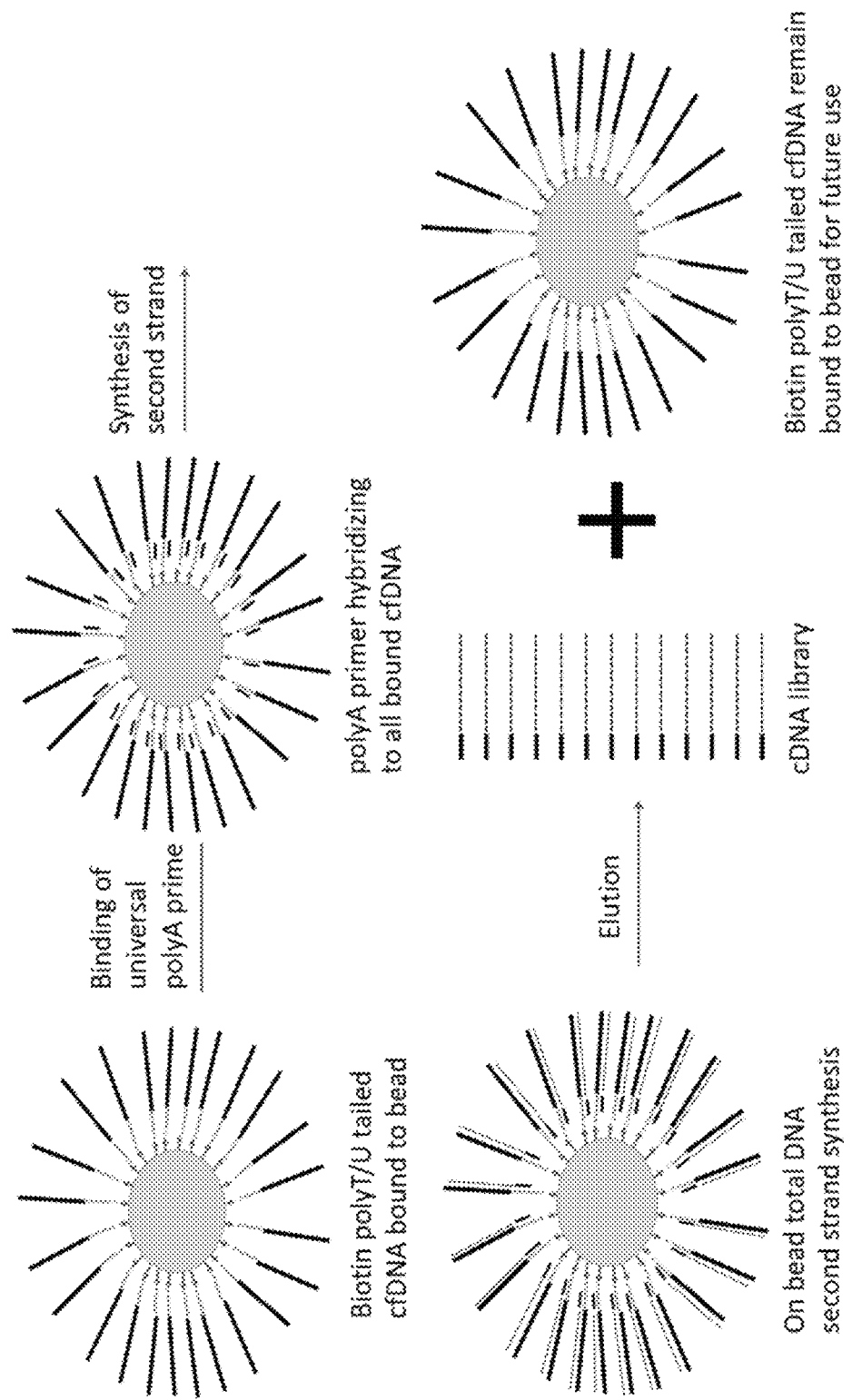
FIG. 3 illustrates the use of isolated nucleic acids for assays with a universal primer to amplify the total nucleic acids. Once the polyA primed second strand cDNA is synthesized on the beads and then eluted from the beads, the tailed DNA remains bound to the beads and can be used for additional reactions.

In certain embodiments, universal primers can be used to synthesize the total DNA or RNA using the isolated nucleic acids bound to the surface of a solid support. As an example illustrated in FIG. 3 and FIG. 27, a polyA universal primer can be used to bind to the tag such that the total nucleic acids bound to the surface of a bead are amplified. The synthesized DNA can be eluted to obtain, for example, a cDNA library, while the tagged nucleic acids remain bound to the surface of the bead and can be used for other reactions.

One of the advantages of the disclosed technology is that the original isolated nucleic acids remain bound to the solid support via the affinity or covalent binding of the tag and can be reused for multiple reactions. This allows all subsequent copies initiated from the original nucleic acid templates, thereby providing an inexhaustible source that also minimizes any errors introduced by amplification or use of immortalized cell lines for production of nucleic acids of interest.

Figure 27A:
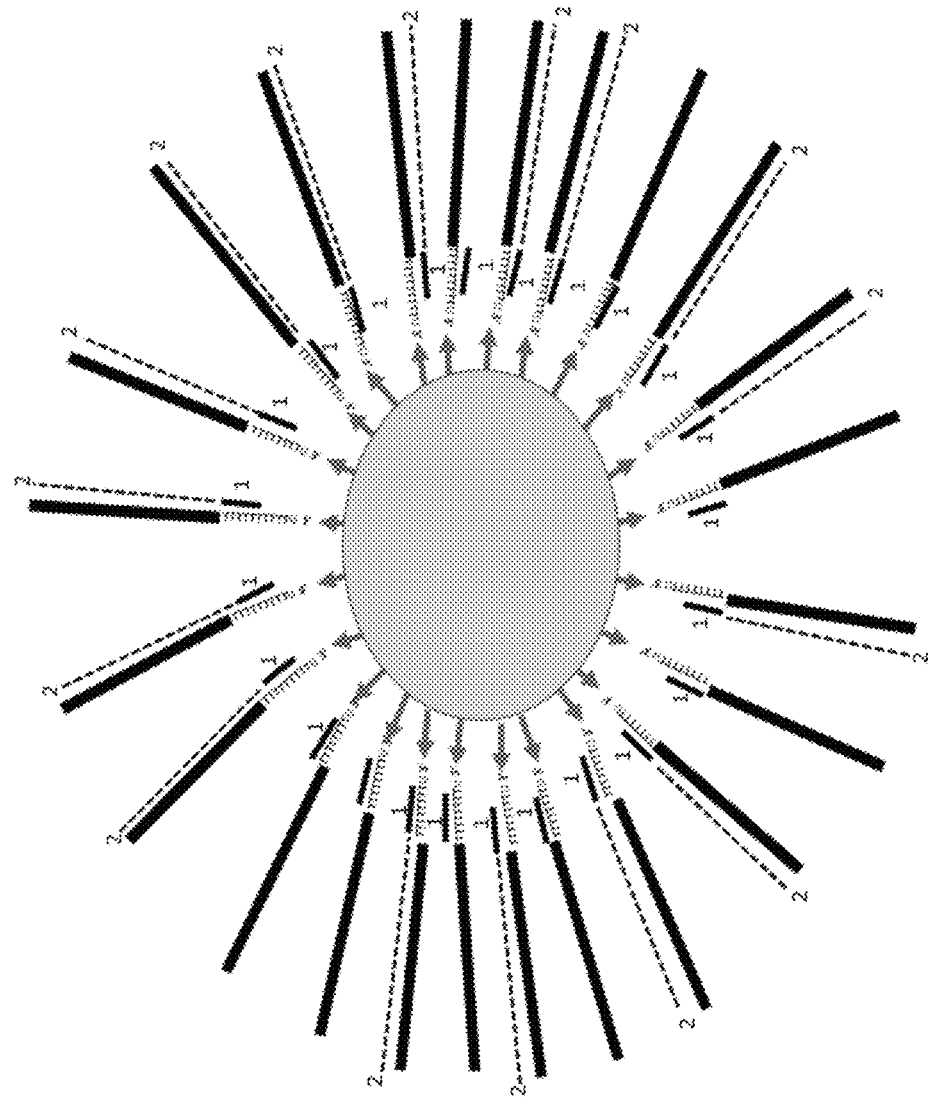
FIGS. 27A-27C illustrate the use of isolated nucleic acids in various cRNA applications.
Figure 27B:
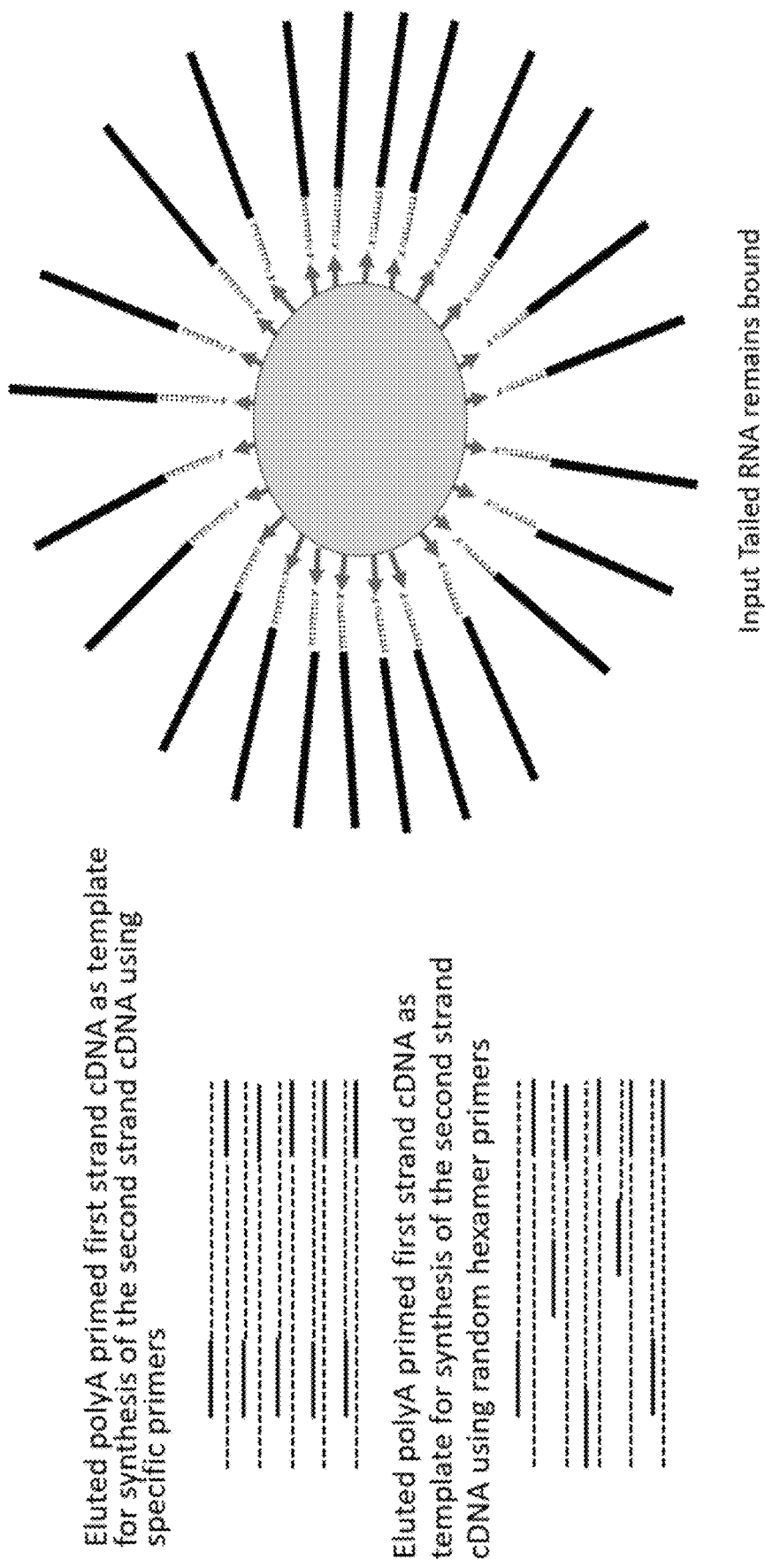
Figure 27C:
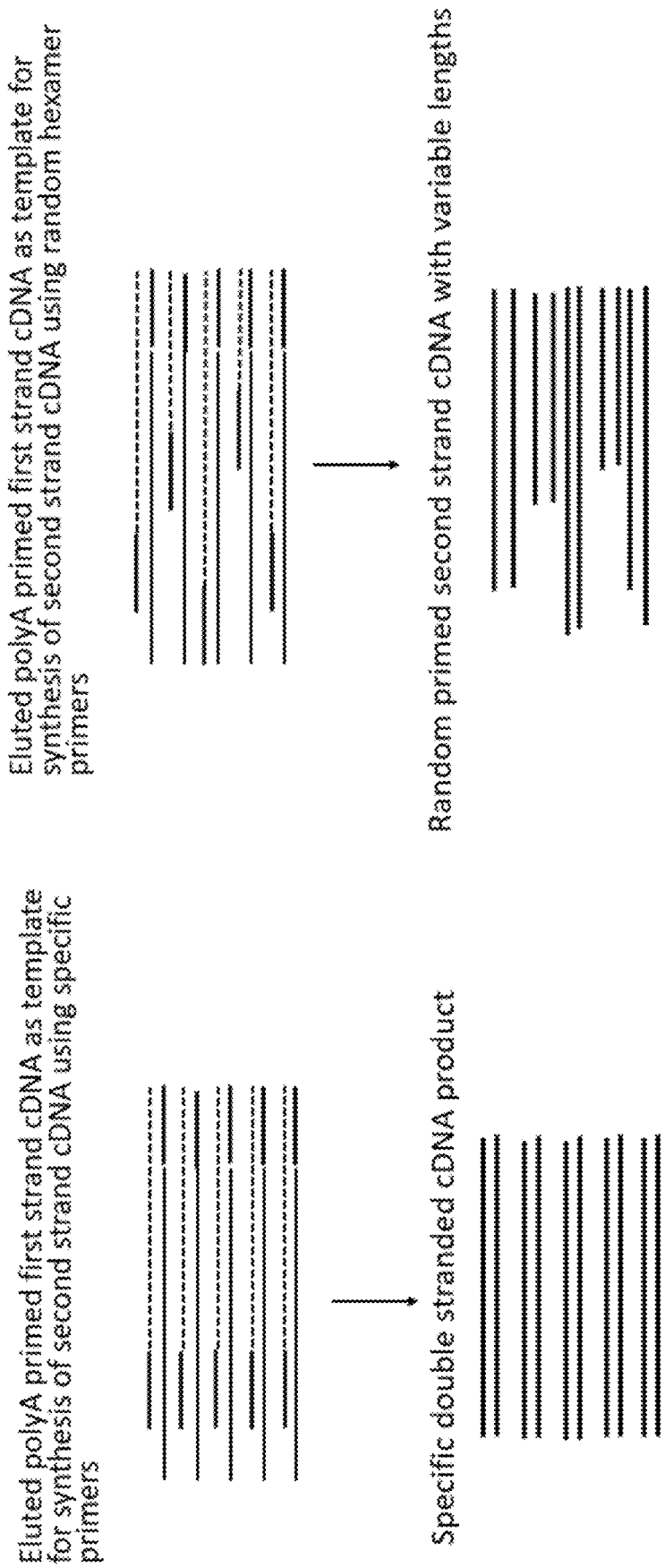

In certain embodiments, sequence-specific primers can be used to synthesize DNA or RNA fragments of interest using the isolated nucleic acid bound to the surface of a solid support as templates. Additionally, sequence-specific primers can be used to obtain a gene pool of desired nucleic acid targets. As illustrated in FIG. 4 and FIG. 27, in this type of assays, not the total nucleic acids but only the nucleic acids of interest are synthesized by specific binding of primers to selected sequences. Therefore, sequence-specific primers can be used to obtain various genomic information such as detecting the presence of certain mutation(s), polymorphism(s), or genotype(s).

In some embodiments, disclosed herein is a method of determine the presence of one or more point mutations or polymorphisms comprising the steps of directly isolating nucleic acids from a biological sample as disclosed herein to obtain single-stranded nucleic acids bound to a solid support, performing a hybridization assay on the solid support using one or more sequence-specific primers, detecting the presence of one or more synthesized nucleic acids derived from the one or more sequence-specific primers, thereby to confirm the presence of the one or more point mutations or polymorphisms.

The disclosed technique also has the advantage of not requiring multiple assay steps, target capture based hybridization or multiple rounds of PCR to replicate nucleic acids retained in a gene pool. As an example illustrated in FIG. 5, sense-strand primers and anti-sense strand primers can be used to synthesize sense-strands and antisense-strands using the isolated single-stranded nucleic acids bound to a solid support as templates. Subsequently, the eluted sense-strands and antisense-strands are annealed at a relatively low temperature to obtain the double-stranded nucleic acids without performing any amplification step that may require subjecting the nucleic acid sample to a high temperature.

Figure 5B:
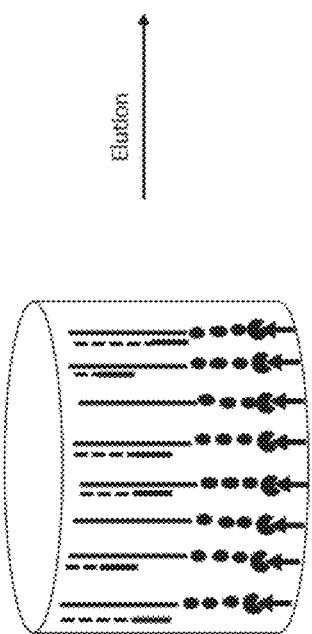
FIGS. 5A-5D illustrate synthesis of sense-strands and antisense-strands to obtain the desired DNA fragments.
Figure 5A:
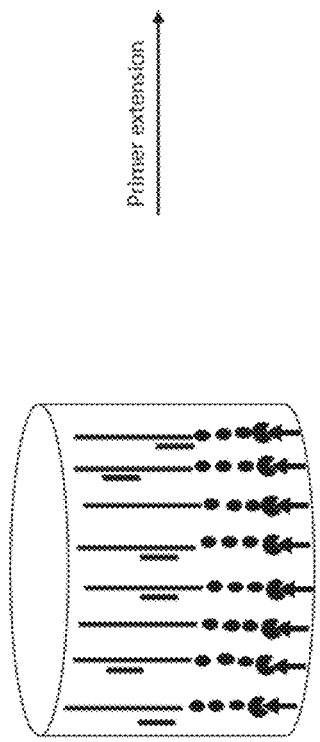
Figure 5D:
Figure 5C:
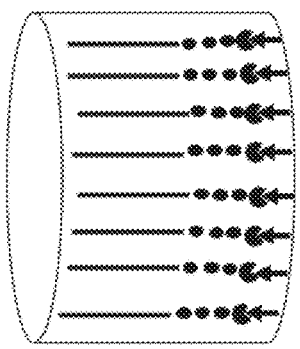

Specifically, binding of the 3' end of single-stranded DNA or RNA allows for standard cDNA reactions to occur. These reactions are well known in the art. They rely upon using single-stranded DNA/RNA serving as the binding template for a complimentary synthetic oligonucleotide primer. These reactions typically are carried out at much lower temperatures than PCR or other competitive hybridization assays. In some embodiments, the assay is performed using DNA Polymerase I at room temperature but can be performed at a range of temperatures according to the enzyme and manufacturers recommendations such as from 16° C. to 42° C. Any enzyme that can extend a template bound primer to make a complementary strand of DNA can be used for this step. Some examples of the enzyme include *E. Coli* DNA polymerase, Klenow Fragment, T4 DNA polymerase, T7 DNA polymerase, phi29 DNA polymerase, BST DNA polymerase, and BSU DNA polymerase. At this stage, sequence-specific primers, random primers, or polyA primers can be used to create the cDNA. PolyA primers bind to the 3' poly T/U tail and make a copy of all bound strands producing a copy of each bound strand. Specific and random primers will bind to distinct locations downstream of the polyT tail. As used herein, a random primer refers to a primer which binds to a random location in a nucleic acid sequence. FIG. 5A illustrates the use of sequence-specific sense-strand and antisense-strand primers. FIG. 5B illustrates primer extension produces cDNAs of varying lengths on each strand, including both the sense and antisense strands. FIG. 5C shows that the synthesized cDNA can be eluted using techniques known in the art, such as NaOH treatment, heat, or other elution buffers. The eluted cDNAs are removed from the assay vessel containing the single-stranded DNA/RNA remains bound to the solid support, which can be reused for other assays. As shown in FIG. 5D, the recovered cDNA sense and anti-sense strands will then re-hybridize based on complementary overlapping sequence. These overlapping sequences can be defined by the use of specific primers to allow for tuning the length of DNA required for downstream reactions. This step also serves as a means to increase the Tm that will limit primer dimers and non-specific products in downstream reactions. These downstream reactions as illustrated in FIG. 6 show the use of the re-hybridized DNA strands as templates to fill in the sequences on the 3' ends of both partner molecules producing a double stranded DNA molecule that now contains the full genomic sequence of interest as well as adapter sequences on both the 5' and 3' ends of each DNA strand.

The annealed sense and antisense strands can be further extended and/or used in additional assays with or without adapters, barcodes, or random primers. Some of the example applications are disclosed below. However, one skilled in the art would understand that other nucleic acid manipulation, hybridization, and sequencing strategies can be adopted to be used with the technology disclosed herein.

Figure 6:
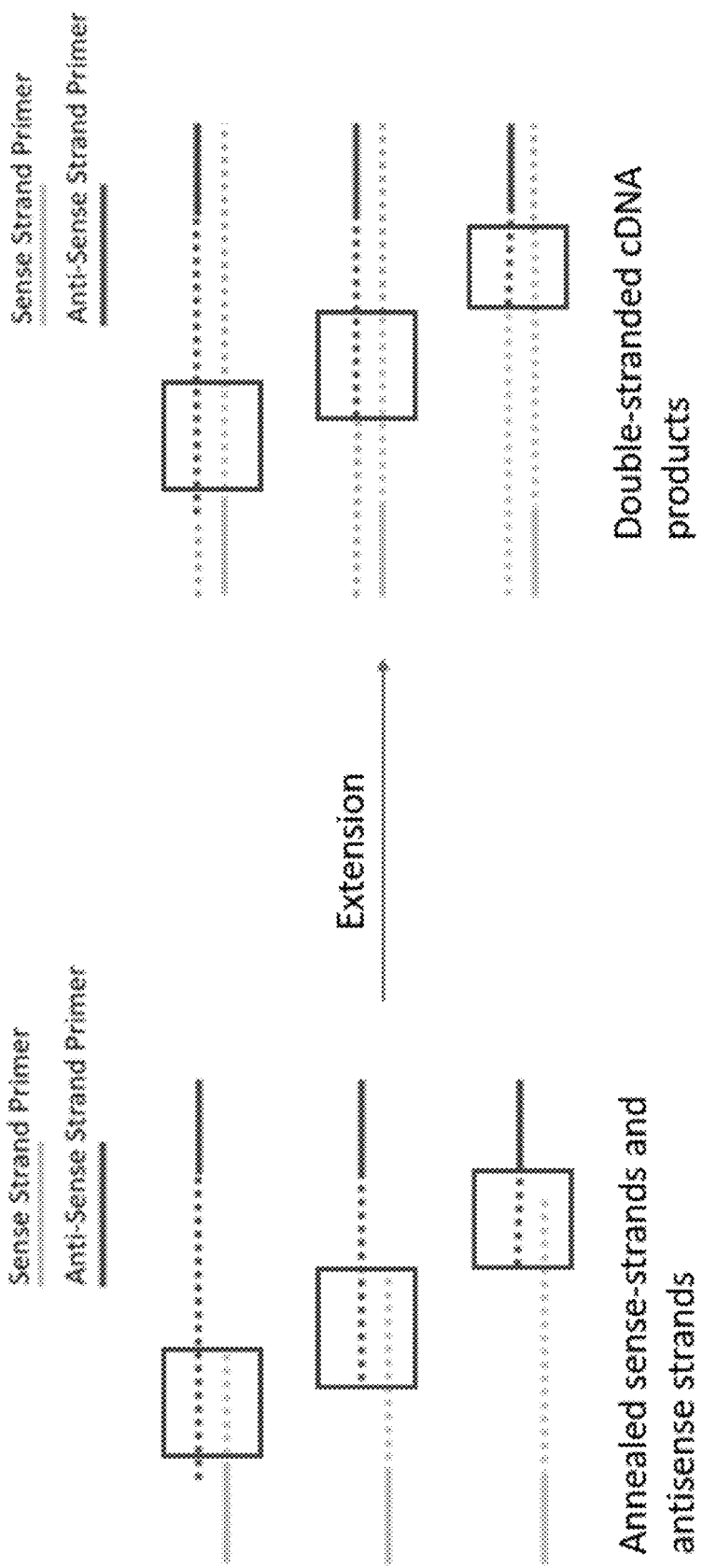
FIG. 6 illustrates extension assay to obtain double-stranded cDNA products from the annealed sense and anti-sense stranded. The complementary genomic sequences for annealing are shown in boxes, and the extended sequences are shown as gray dotted lines.

In one example illustrated in FIG. 6, the annealed sense and antisense strands can be extended to obtain double-stranded cDNA products. With the sense and anti-sense strands re-hybridized, the overlapping sections can then be extended to fill in the 3' ends on each strand. This is depicted as the dotted lines in FIG. 6. This extension reaction can happen using the same process disclosed for cDNA synthesis or using PCR. For either the cDNA or PCR approach no oligonucleotide primers are added. Only the enzyme, buffers and dNTPs are added. This will extend the hybridized DNA strands on the 3' to the end of the 5' portion of the opposite complementary strand. This reaction is carried out for a limited number of cycles (ideally 1-5 cycles).

Figure 24A:
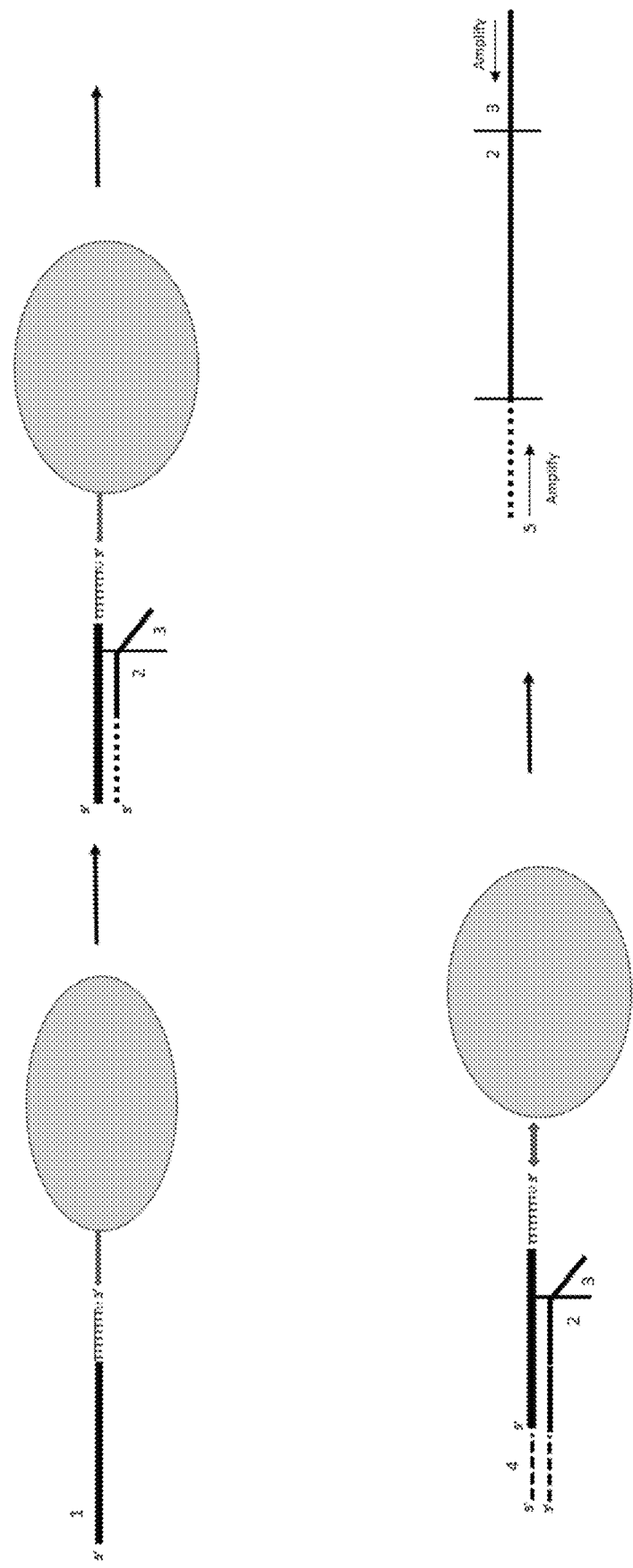
FIGS. 24A-24B illustrate on bead ligation for specific primed cDNA product (FIG. 24A) and polyA primed cDNA product (FIG. 24B).
Figure 24B:
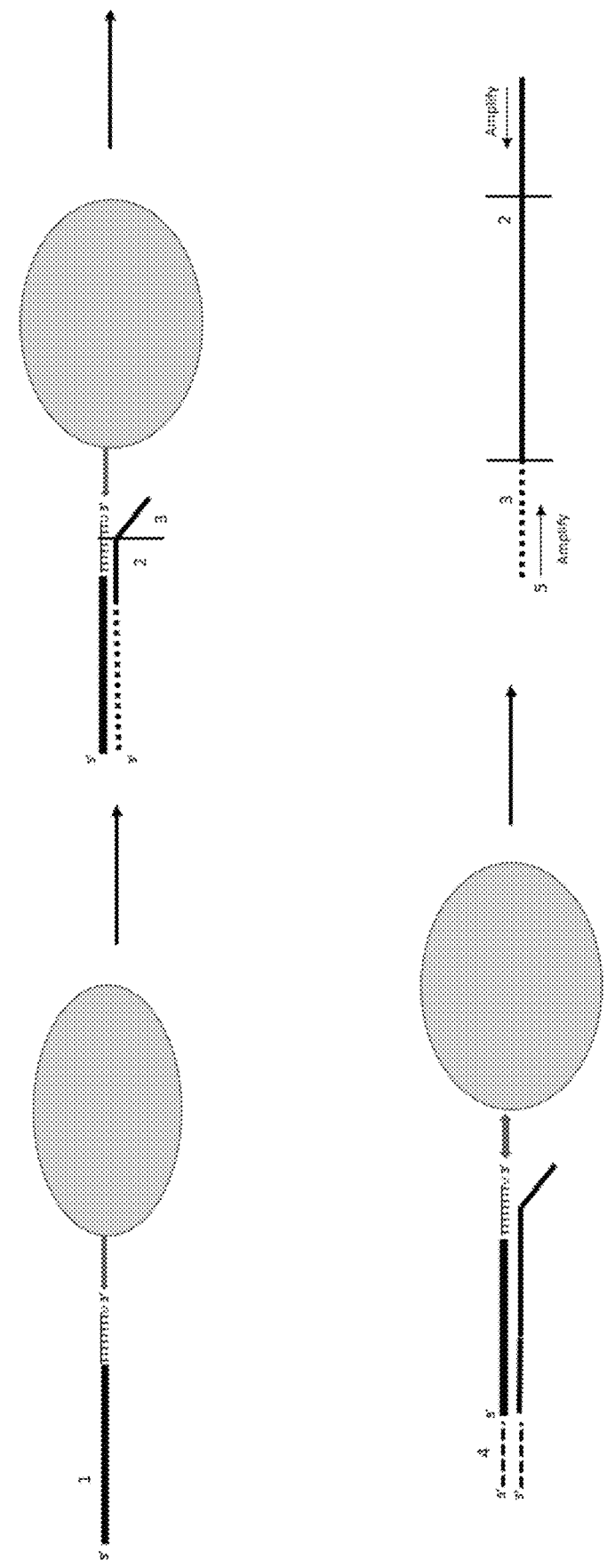

Also disclosed are alternative methods for creating DNA libraries bound to beads. Using a stubby adapter tagged specific primer or a polyA primer for cDNA synthesis on beads, ligation using standard double stranded Y adapters can be performed (FIG. 24). Due to the lack of phosphate on the 5' end of the bound DNA molecule, this location does not serve as a site for ligation. But the 5' phosphate on the branched Y adapters ligates to the newly created 3' end created by Klenow Exo-that adds the requisite additional A base for ligation. This step leaves the initially bound DNA molecule intact but creates a new cDNA molecule with a full length i7 adapter bound to its 3' end and an i5 stubby adapter at its 5' end. The cDNA product can then be amplified with a nested primer set consisting of indexed i5 adapter and outer PCR primers targeting the i7 end of the molecule. The IDT i5 adapters can be used with Illumina NGS PCR primer set.

The bound, isolated nucleic acids can be replicated or reinterrogated for new or additional regions of interests. Allowing initial assay preparations to guide decision on further and more in-depth analyses. This method can serve to place samples into cohorts based on genomic markers. Examples of DNA-based assays include, for example, whole genome sequencing, targeted panel sequencing, hot spot sequencing, methylation sequencing, non-invasive prenatal screening (NIPS), and tumor mutation burden (TMB). RNA-based assays include, for example, whole transcriptome, miRNA sequencing, lncRNA sequencing, fusion detection assays, and T-Cell Repertoire (TCR) sequencing.

Use of the Isolated Nucleic Acids in NGS

Figure 7:
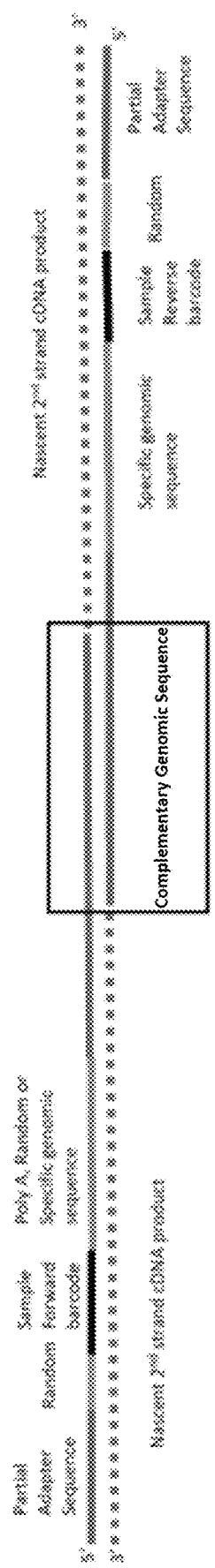
FIG. 7 illustrates that additional tagging strategies can be adapted to the disclosed technology. The adapter is placed on the 5' end while the random sequence and barcode can be placed in any desirable order when attached to a universal or specific primer. The random sequence can serve as a Unique Molecular Identifier (UMI) and be used to determine PCR duplication. Although the genomic sequence may appear multiple times, the UMI allows identification of the genomic products derived from a unique molecule and not from PCR duplication.

Using the PCR approach, the reaction can be stopped after this step and primers containing the partial tag sequence, index and necessary sequencing for processing on Next-Generation Sequencing (NGS) instrumentation can be added, as illustrated in FIG. 7.

Figure 8:
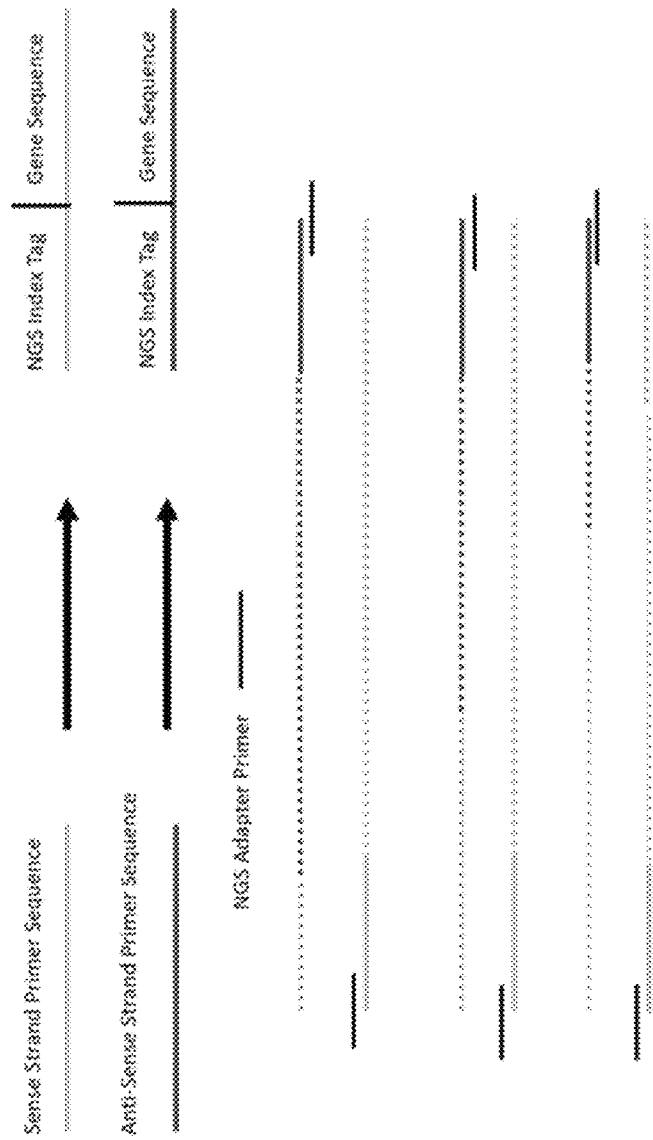
FIG. 8 illustrates using NGS primers for amplification of cDNA products.

In certain embodiments, the nucleic acids directly isolated from a biological sample as disclosed herein can be used for NGS. FIG. 8 illustrates that the addition of NGS specific primers allows for amplification of the tagged 5' end of the double stranded cDNA products as disclosed above. This reaction will provide the means for sample identification via barcoding of pooled samples and processing on current commercially available NGS instruments.

Various tagging and indexing strategies used for NGS can be adapted for use with the disclosed technology. The primer sequences illustrated in FIG. 9 display one set of options for the tag sequences that would be included on all primers used in the reactions disclosed herein. The 3' end contains polyA, random or specific sequence primers, which has a length of at least 6 bases and allows extension of the complementary strand of the template. Directly upstream of the complementary sequence is an optional sample barcode, followed by a random 8-base sequence that serves as a unique molecular identifier. The barcode sequence is usually at least 4 bases for the forward and reverse strands and can be used to identify the starting material as DNA, RNA, miRNA or any other specific type of nucleic acid species. The random 8-base sequence is intended to identify truly unique molecules of cDNA produced by the assay and serves the purpose of removing duplicate reads generated by PCR or the NGS instrument which can affect the allele frequency calculation accuracy for rare variants or gene expression values such as those found in many cancer samples. The random 8-base sequence can be shorter or longer, usually at least 4 bases long. A partial adapter sequence, usually at least 20 bases, is on the 5' end and serves as the means of PCR amplification. The partial adapter sequence can be used to add a priming site for downstream PCR as well as addition of a tag that can be used by downstream technologies for detection applications such as NGS technologies from Illumina, Ion Torrent, or any other commercial instrument employing sequencing as a means to decipher specific genetic code. The elements of the primers can be rearranged in different configurations depending on the assays and desired products. Non-limiting examples of the primer configurations are shown in FIG. 10. Examples included herein utilize Illumina short read NGS technology including protocols and adapters specific to this technology. The technology is flexible and customizable to be used in any NGS platform both short and long read, with and without amplification and with any adapter and primer sequences required. In some embodiments, the isolated nucleic acids bound to the solid support can be used in single molecule sequencing such as PacBio SMRT sequencing and Oxford Nanopore sequencing.

Figure 9:
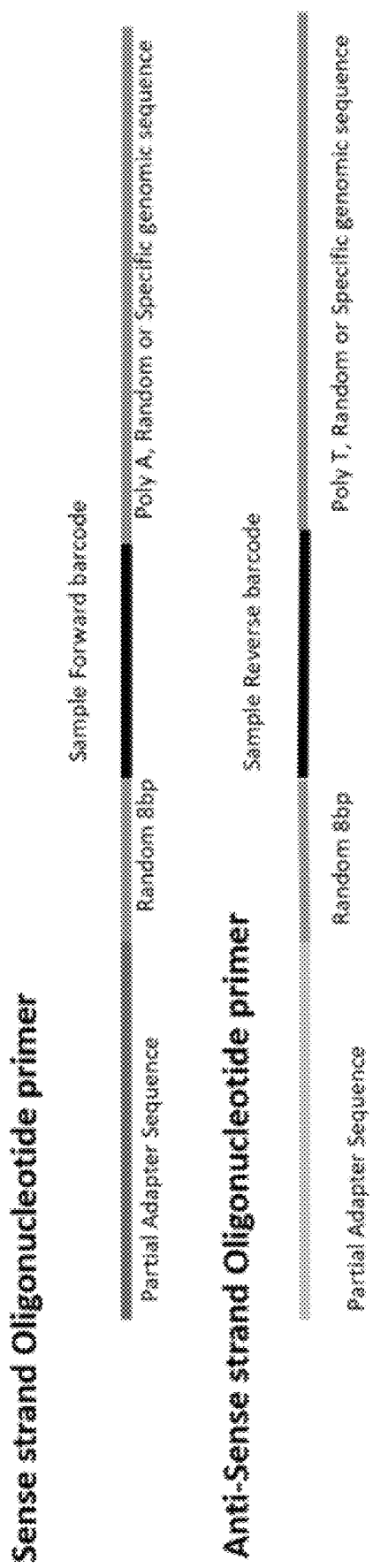
FIG. 9 shows an example design of the configuration of sense-strand and antisense primers.
Figure 10:
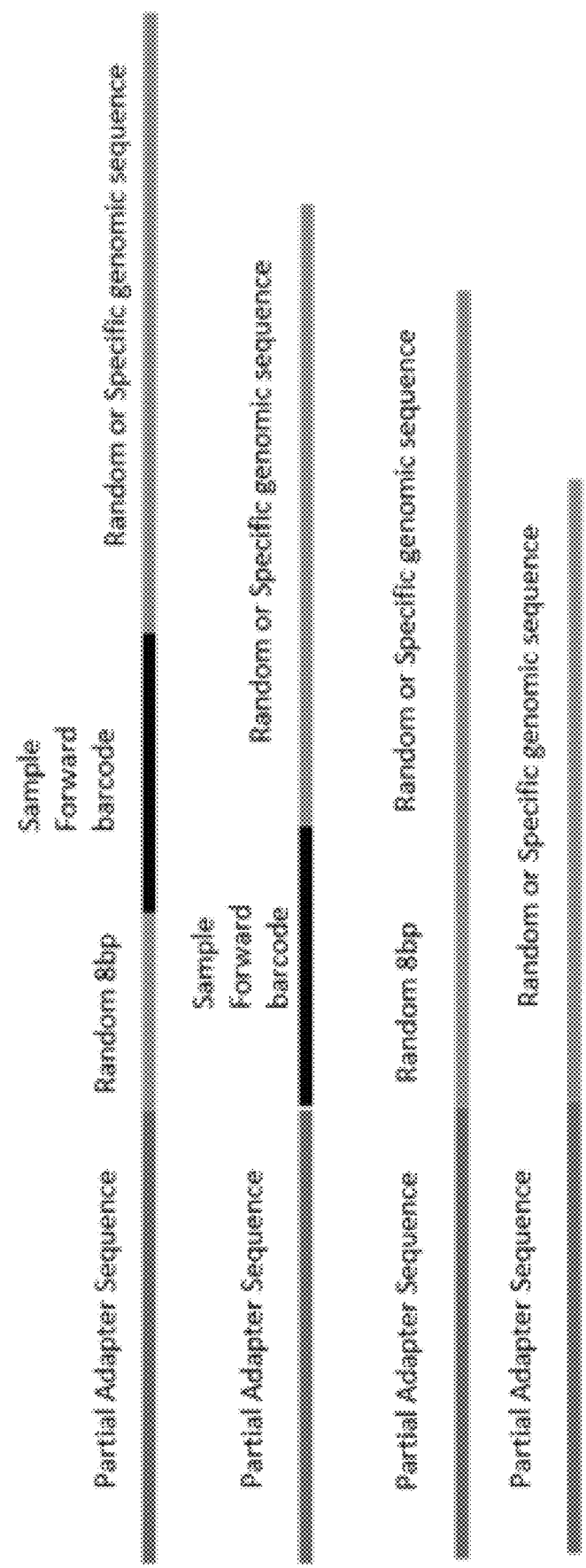
FIG. 10 shows various configuration of the primers.
Figure 11A:
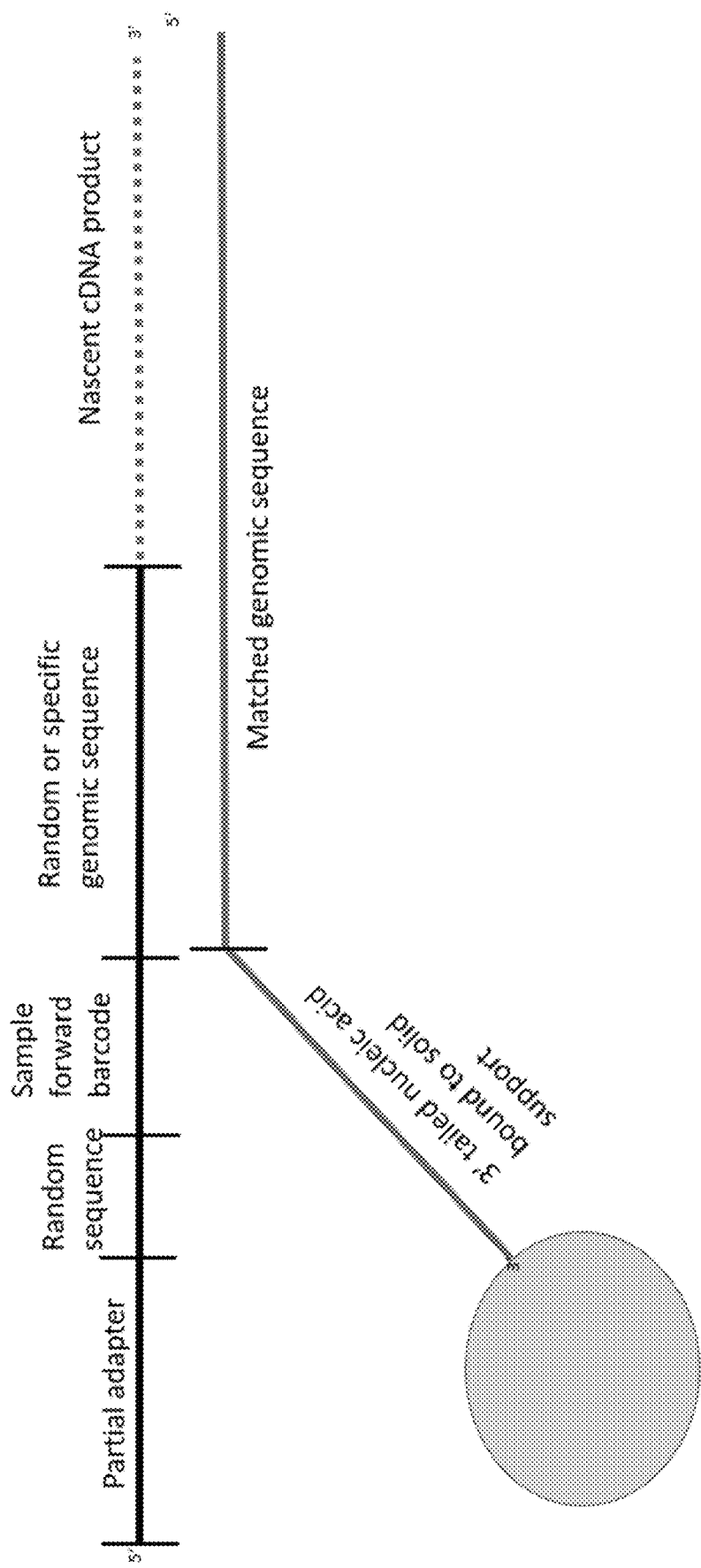
FIGS. 11A-11C show examples of the reaction schema to obtain PCR products from an intermediate cDNA product.
Figure 11B:
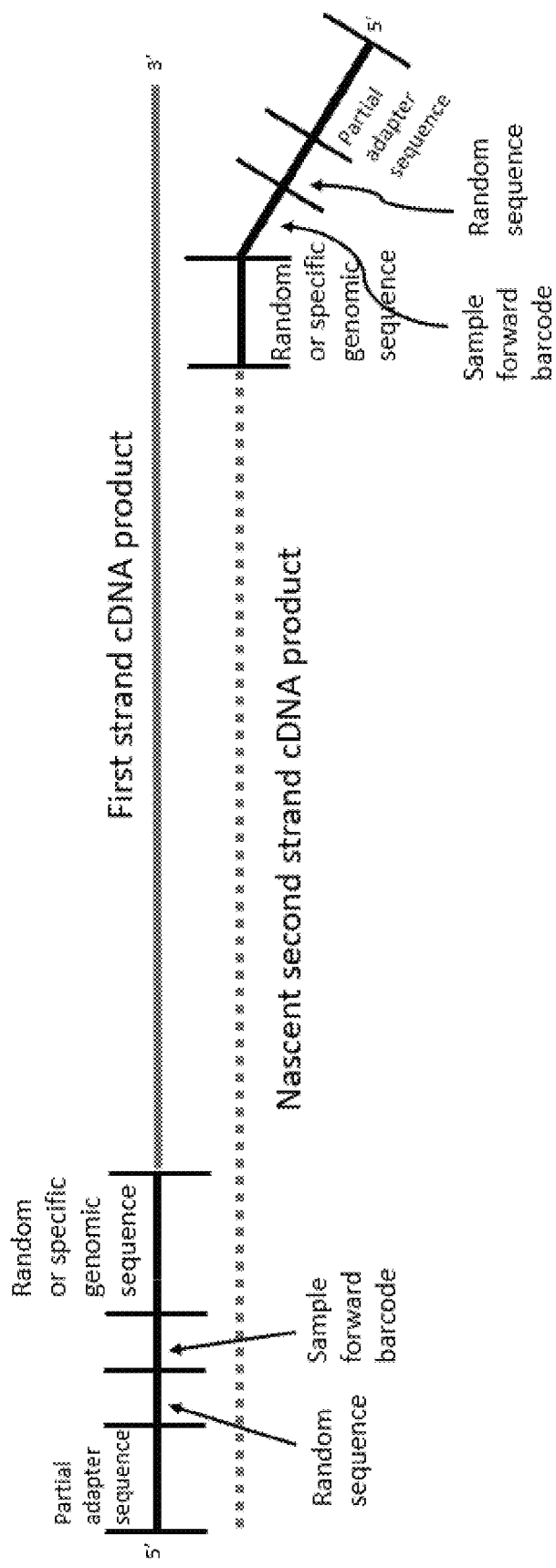
Figure 11C:
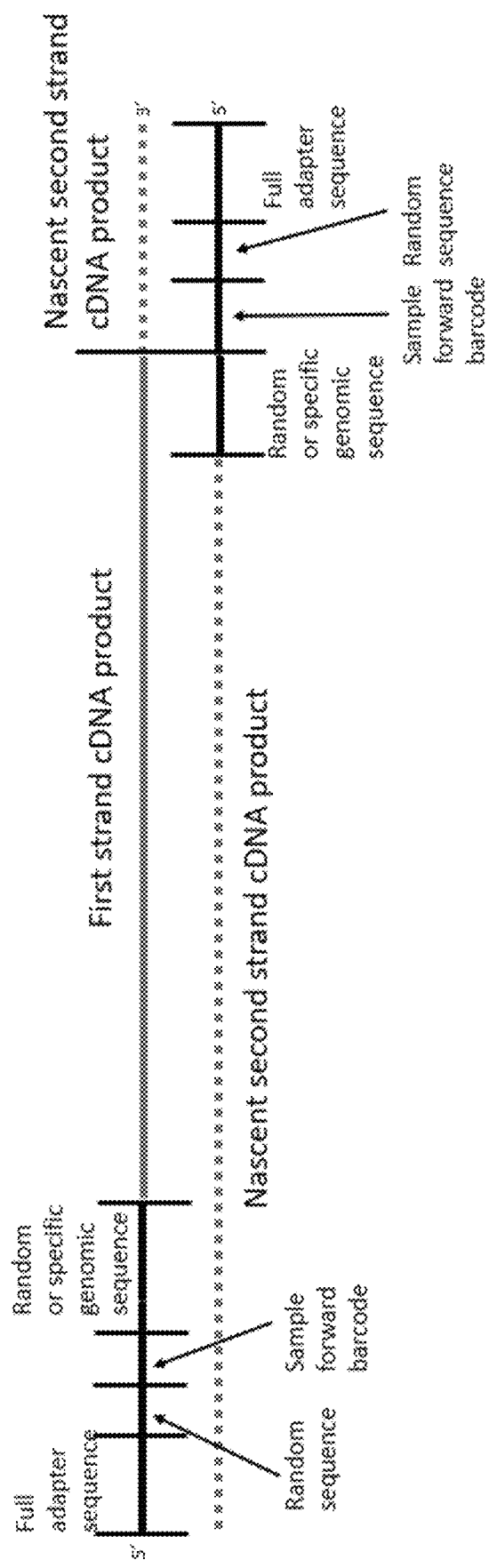

FIG. 11 illustrates the use of the primers depicted in FIG. 9 in a reaction schema. FIG. 11A shows using the single-stranded nucleic acid bound to a bead as a template, a nascent cDNA strand is obtained by binding and extending only the forward primer (sense-strand primer) to the template. This step can be carried out with different reactions, for example, a single cycle reaction or a multiple cycle reaction using only the forward primer, any reaction using nested primers with or without the nongenomic tag sequences included, or a PCR-based reaction using both forward or reverse primers. The newly produced cDNA strand is then eluted from a solid support, such as streptavidin beads, e.g., by NaOH or heat dissociation of the bound cDNA. The eluted cDNA strand can serve as the template for producing a second strand using the reverse primer (antisense-strand primer), thereby to obtain an intermediate double-stranded cDNA having the partial adapter sequences attached to the 5' end, shown in FIG. 11B. The production of the intermediate double-stranded cDNA can be performed directly on the first strand cDNA eluted from streptavidin beads and random or specific primers can be used for this step. PolyA tailing can be performed directly on the first strand cDNA eluted from streptavidin beads. For example, polyA biotin tailed product can be bound to the streptavidin beads and bound cDNA can be synthesized using polyT primers. Alternatively, cDNA can be synthesized in solution using polyT primers. The intermediate double-stranded cDNA can be purified by, for example, solid phase reversible immobilization (SPRI) magnetic beads, and used for PCR amplification using primers binding to the partial adapter sequences. Alternatively, PCR can be performed directly on the biotinylated single-stranded cDNA bound to the streptavidin beads. The PCR primers can incorporate the complete adapter sequence for use in downstream applications such as NGS data generation. These PCR primers can be nested primers and/or customized for use with or without the nongenomic tag sequences. For example, the PCR primers can include the sequences for individual manufacturers instrumentation and/or to include index sequences for use in multiplexing samples on various instruments. The total number of the PCR cycles vary based on many factors such as the input and the number of the genomic targets. The PCR products can also be purified using standard protocols such as SPRI beads. FIG. 11C shows the structure of the PCR products.

Figure 12:
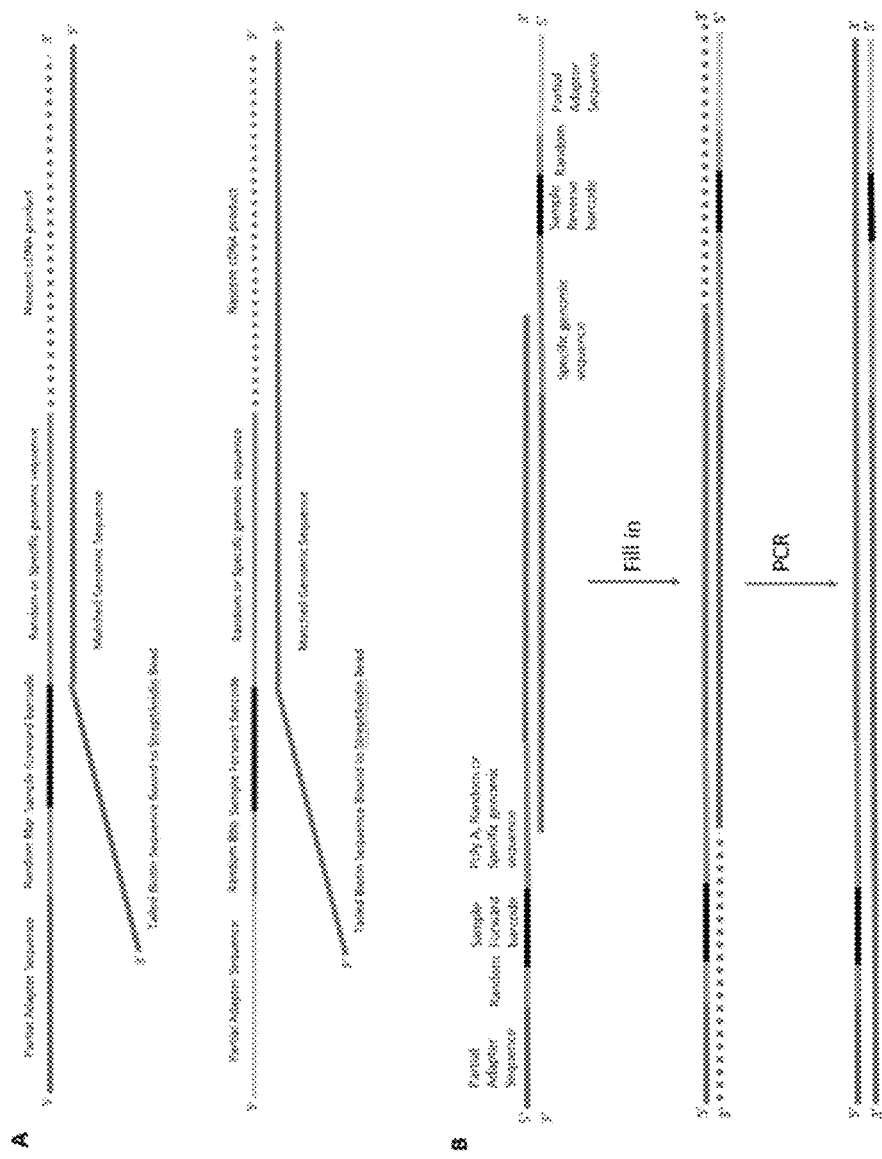
FIG. 12 shows another example of the reaction schema to obtain PCR products from an intermediate cDNA product.

FIG. 12 illustrates the use of the primers depicted in FIG. 9 in another reaction schema. FIG. 12A shows using the single-stranded nucleic acid bound to a bead as a template, nascent cDNA strands are obtained by binding and extending both the forward and reverse primers (sense-strand and antisense-strand primers) to the template. The single-stranded cDNAs are eluted and the complementary strands are annealed to form an intermediate double-stranded cDNA. The intermediate can be amplified by PCR using primers binding to the partial adapter sequences. The first cycle of PCR fills in the 5' overhanging sequences on the complementary annealed cDNA and the subsequent PCR steps result in PCR products having the full-length adapter sequences, as shown in FIG. 12B.

Captured Nucleic Acid Complex

In yet another aspect, this disclosure relates to a captured nucleic acid complex obtained by the technique disclosed herein. The capture nucleic acid complex comprises a solid support such as a bead or a plate, and a plurality of isolated, purified nucleic acid fragments, each fragment having a 3' end bound to a polymeric tail, and each polymeric tail is bound to a surface of the solid support. The polymeric tail comprises one or more NTPs, dNTPs or ddNTPs that are modified such that the polymeric tail can be attached to the surface of the solid support via affinity binding or covalent binding to the binding partner coated on the surface, as disclosed above. The nucleic acids can be DNA or RNA, and can be double-stranded or single-stranded. Other features of the complex are disclosed above in various embodiments, for example, either the polymeric tail or the nucleic acid fragment comprises a priming location to bind a universal primer or a specific primer for copying the nucleic acid fragment by, for example, amplification (including linear amplification (LAMP) and PCR amplification), and non-exponential single or multi-cycle cDNA synthesis. When a universal primer is used, all nucleic acid fragments and the entire sequences of the nucleic acid fragments are copied. When one or more specific primers are used, only selected nucleic acid fragments are copied. Also, when one or more specific primers are used, partial or entire sequences of selected nucleic acid fragments are copied, depending on the priming location.

The captured nucleic acid complex disclosed herein has various applications in genetic research. For example, a gene pool, a biobank or a biorepository can be generated by a plurality of the complexes. Due to the stability during long-term storage and the capacity for repeated use, one or more captured nucleic acid complexes can serve as a gene pool to archive nucleic acids of interest. Similarly, one or more captured nucleic acid complexes can serve as a biobank or biorepository for an individual subject or a population of subjects. For example, the nucleic acids from one individual can be captured and stored on one or more complexes at different time points such that genetic comparisons can be made at various time points, e.g., different age periods to detect a disease such as cancer, or before and after treatment for diagnosis and/or prognosis. In another example, the nucleic acids from a population of different subjects can be combined, captured and stored on one or more complexes to establish a threshold for detecting a disease state and/or for comparing the genetic information of a healthy subject or population with that of a diseased subject or population. In certain embodiments, one or more captured nucleic acid complexes comprise substantially all nucleic acid fragments present in a biological sample. For example, the one or more captured nucleic acid complexes comprise at least 50%, at least 60%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of all nucleic acid fragments present in the biological sample. In certain embodiments, the biobank or gene pool comprises one or more captured nucleic acid complexes comprising substantially all genomic DNA such as at least 50%, at least 60%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the entire genome. In another example, the captured nucleic acid complex can simplify certain existing technologies that rely upon copying or amplifying genetic materials such as DNA and RNA, for example, PCR, rtPCR, and NGS. In yet another example, the captured nucleic acid complex can be used as a long-term storage of nucleic acid samples due to its demonstrated stability and capability of repeated uses.

The novel technique disclosed herein allows for the production and application of the capture nucleic acid complexes. Traditional nucleic acid extraction, isolation and purification procedures are labor intensive, require multiple pieces of laboratory equipment and do not have desired specificity. The standard practice utilizes ionic charge as a means for interaction of nucleic acids to either microsphere beads or filters in spin columns. This interaction is not specific for nucleic acids or specific for the location or orientation of the nucleic acid molecules. The method disclosed herein provides for nucleic acid binding in a single 3' orientation. These properties allow for direct affinity or covalent binding which provides the nucleic acid molecules to be used directly in multiple molecular biology applications, such as cDNA synthesis, primer extension, regeneration of original input material and PCR based methodology.

Assays performed on the bound nucleic acid molecules can produce materials suitable for PCR and NGS based analysis. Due to the defined 3' orientation of single stranded molecules, NGS assay can be performed without ligation, multiple PCR stages or complicated targeted capture hybridization steps. The completed NGS library can be processed in fewer steps, with far less manipulation providing a more robust system without the aforementioned methods that contribute to known errors and shortcomings in the standard NGS sample preparation assays.

The advantages of the disclosed technology are demonstrated by the description above and the following examples. Some examples of these advantages include but are not limited to: specific binding of DNA/RNA based on affinity or covalent chemistry, DNA/RNA bound with a long tail attached to the 3' end allowing access to the entire genomic sequence, DNA/RNA bound single stranded allowing direct access to the DNA/RNA strand for cDNA reactions, cDNA reactions replacing the need for competitive hybridization assays that are time and temperature sensitive, and the input DNA/RNA being covalently bound and hence being used multiple times without loss of the original DNA/RNA/cDNA. This will allow for replication of the DNA/RNA/cDNA sample using a simple cDNA synthesis assay. Further, the products from this cDNA assay can be used in PCR, qPCR, ddPCR as well as other NGS assays. Ligation steps are optional but not required for addition of either index or NGS primer sequences. Using primers with index and NGS primer sequences assures that each strand of DNA produced in the assay contains these elements. Ligation is inefficient which means that not every copy of DNA will have the adapters added. This process also forms ligation artifacts such as adapter dimers which affect downstream reactions reducing the yield of the desired products. A single PCR reaction with limited cycles is used in the disclosed technology in comparison to the use of multiple PCR steps with high cycle numbers. Primers are used to specifically target the sense and anti-sense strands which allows for calling of phased variants. Phased variant calling allows for determining which strand a mutation occurs, either the coding strand or non-coding strand. If a variant occurs on the coding strand it will be included in mRNA synthesis and protein translation. If it occurs on the non-coding strand it is a silent mutation that will not affect either mRNA or protein translation. The standard methods using either PCR or capture technology are not able to do this since the adapter ligation is equally likely to bind either end of the DNA molecule which makes strand orientation impossible. The assay is a dramatically simplified reaction process with only a single purification step required post PCR. Standard assays require 2-5 purification steps.

The following examples are intended to illustrate various embodiments of the invention. As such, the specific embodiments discussed are not to be constructed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Materials and Methods

DNA samples used for testing: Synthetic oligonucleotides (IDT, Coralville Iowa) covering the MTHFR genes in exon 7 containing rs1081133 were used for single stranded tailing assays. The sequences of the DNA samples are shown in FIG. 13.

Cell lines: Cancer cell lines BT474, DLD1, HT29 and SKBR3 cells (ATCC) were used. DNA was extracted using Qiagen All Prep kits (Germantown Md.). This DNA was then enzymatically fragmented for 15 minutes at 37° C. followed by purification with SPRI beads using the Kapa Hyper Plus kit (Pleasanton Calif.). Purified DNA was then end repaired following manufacturers recommendations using the Kapa Hyper Plus kit to ensure the 3' ends were able to accept dNTP incorporation.

TdT enzyme, buffer, dNTPs, and ddNTPs were purchased from ThermoFisher (Carlsbad Calif.), NEB (Ipswich Mass.), Roche (Indianapolis Ind.). For experiments using IDT oligonucleotides, each individual oligonucleotide was resuspended in individual tubes from the manufacturer to a concentration of 0.1 nmol.

DNA tailing: 200 ng of DNA was added into a reaction mixture containing 4 µl of 5× Reaction Buffer, 7 µl of 95:5 ratio of unmodified:modified dNTPs, with 1.5 µl of TdT enzyme (25 U/µl) in a final volume of 20 µl. Reactions were carried out at room temperature (20-27° C.) for 1-4 hours. HD780 and HT29 control DNA was used with and without end repair/A tailing.

Example 1: Detection Assays

Taqman qPCR experiments were used to assess the presence of MTHFR gene SNP rs1081133, using Taqman primer/probe set and TaqPath ProAmp mastermix (ThermoFisher). Experiments were carried out on a QuantStudio 6 flex instrument in 384 well format (ThermoFisher). Assays were run using 5 µl of 2× TaqPath ProAmp master mix, 1 µl of Taqman assay by ThermoFisher (Part No: C1202883_20) (www.thermofisher.com/order/genome-database/details/genotyping/C 1202883_20?CID=&ICID=&subtype=) and 4 µl of sample.

Next Generation Sequencing assays were performed using a custom AmpliSeq panel interrogating 80 SNPs across the genome. AmpliSeq reagents and primer pool (Illumina, San Diego Calif.) were run according to manufacturer's protocol and run on a NextSeq 500 NGS instrument using paired 75 bp reads with dual indexing.

Figure 14A:
FIGS. 14A and 14B are the gel images showing TdT mediated tailing of dsDNA from HT29 extracted human cell line DNA.
Figure 14B:
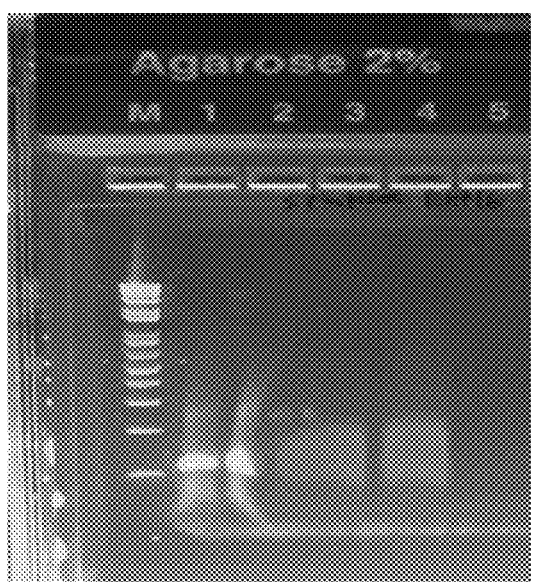

For visualization of tailed and PCR products pre-cast 2% agarose gels (ThermoFisher) were used according to manufacturer's protocols. FIG. 14A is the gel image showing TdT mediated tailing of dsDNA from HT29 extracted human cell line DNA. FIG. 14B is the gel image showing that a poly T/U tail could be added to double-stranded DNA.

For the tailing experiment, 3 oligo controls were run at 3 concentrations (25 U, 50 U, and 100 U) of the TdT enzyme, and all concentrations showed equivalent results.

Example 2: Binding of Tailed Samples

Tailed DNA samples with biotinylated dUTP incorporated into the tail were bound to either streptavidin Beads or to polystyrene plates containing Nuetra-Avidin. Samples were bound with Tris Buffer Saline at pH 7.4. Binding was performed at room temperature (20-27° C.) for 15 minutes in a volume of 200 µl, with 10 ng of tail DNA added, DNA that had not be tailed was added as a control. After binding the supernatant was removed and kept for further analysis. The beads or plates were washed 3 times with 200 µl of TBS buffer, with a final volume of 200 µl of TBS buffer for resuspending beads.

Example 3: cDNA Synthesis

Beads with bound DNA in a 96 well plate format were added to a magnetic stand to pellet the beads. TBS buffer was removed from beads. A first strand master mix containing; 5 µl 10× React 2 Buffer, 1 µl of 10 mM dNTP mix, 1.25 µl of DNA Pol I enzyme (25 U/µl), 42.75 µl of water (ThermoFisher), with 1 µl of Poly A primer (IDT, Corralville Iowa). This was added directly to the beads at room temperature (20-27° C.) for 30 minutes. The plate was added to a magnet, the supernatant was removed and the beads were washed 3 times with 200 µl of TBS. 100 µl of 0.2 M NaOH was added to the beads and mixed. This solution was held at room temperature (20-27° C.) for 5 minutes. The plate was returned to the magnet and the eluted DNA was removed in the supernatant. This eluted cDNA can then be used in qPCR and NGS experiments.

In another experiment, the IDT oligo was tailed and bound to beads followed by cDNA synthesis using DNA Pol I. The eluted cDNA products and beads were run on qPCR. Both beads and supernatant amplified, as well as the control reaction supernatant, leading to the conclusion that high temperatures can cause interruption of biotin-streptavidin binding. A total of 6 samples were run with 2 different specific primers for cDNA synthesis.

Example 4: Taqman qPCR Experiments

Experiment 1: Adding beads with bound DNA directly as well as eluted cDNA into the qPCR reactions produced the appropriate heterozygous call on for the fragmented and tailed HT29 sample. The tailed samples showed amplification and correct SNP genotyping calls, whereas the untailed samples did not amplify. Table 1 below shows results for eluted cDNA product.

TABLE 1

|  | Bead Supernatant | HT29 Bound | HT29 Stock |
|---|---|---|---|
| Ct Value | Undetermined* | 19.2 | 13.3 |
| Genotype | Undetermined* | Heterozygous** | Heterozygous** |

*Undetermined means no amplification was observed. This shows that there was no random or background amplification or contamination.
**Heterozygous means both alleles are present, showing that the bound provided the same answer as the stock DNA in solution. Taken together with the undetermined, it shows that the process of binding to the bead was specific and the assay can be performed on the bead.

Experiment 2: HT29 DNA was spiked into an equal volume of serum and run according to the TdT tailing protocol: Twenty-five units of enzyme was added in 1× supplied buffer, and mixed with 10 nmol dTTP and 0.1 nmol dUTP Biotin. HT29 DNA without serum was run as a control. Both samples were tailed for 4 hours at room temperature and subsequently bound to streptavidin beads by adding the tailing reactions to streptavidin beads in 1×PBS. The beads were incubated with the samples at room temperature for 30 minutes and then washed 3 times in 1×PBS. Taqman qPCR results using beads as input showed similar values for both serum and standard buffer with HT29 DNA.

Figure 15:
FIG. 15 is the gel image showing the PCR products from beads with bound tailed HT29 DNA and MTHFR synthetic oligonucleotide. For Lanes 3 and 4, only 1 PCR product was produced due to the oligonucleotide representing a single genomic sequence. Lane 1 represents HT29 DNA untailed beads, lane 2 represents HT29 tailed DNA bound to beads, Lane 3 represents MTHFR oligonucleotide positive control, and Lane 4 represents MTHFR oligonucleotide tailed bound to beads.

Experiment 3: Beads with bound tailed HT29 DNA and MTHFR synthetic oligonucleotide were added directly into the first PCR step of the AmpliSeq assay and PCR was performed according to Illumina's protocol (support.iliumina.com//downloads/ampliseq-for-illumina-custom-and-community-panels-reference-guide-1000000036408.html). PCR products were then visualized on a 2% agarose gel, as shown in FIG. 15. The PCR is an 80 plex that will produce products of varying lengths. For Lanes 3 and 4, only 1 PCR product will be produced due to the oligonucleotide representing a single genomic sequence.

Figure 16:
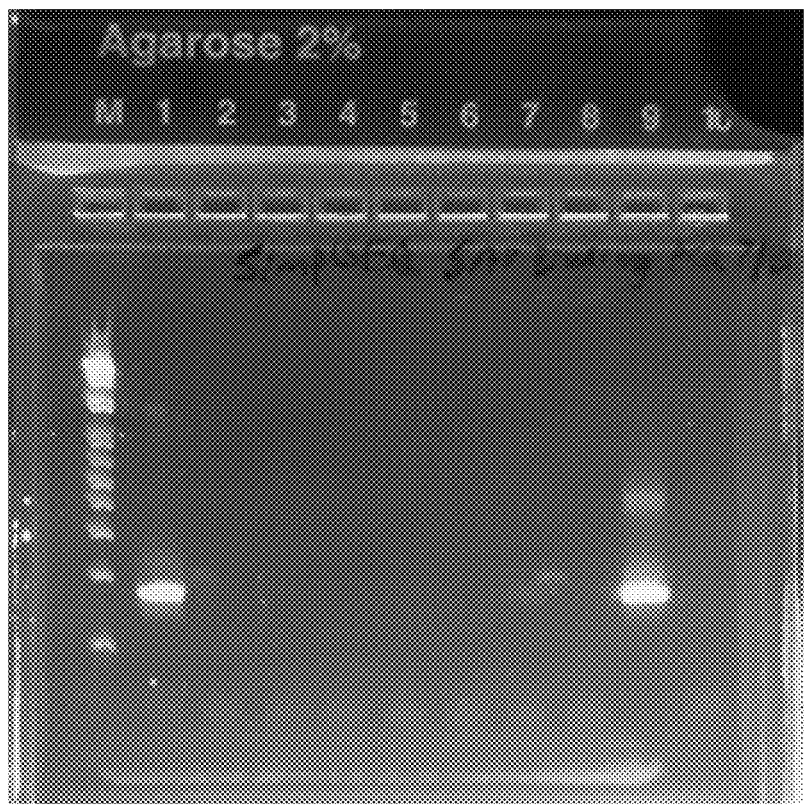
FIG. 16 is the gel image showing the PCR products from beads and supernatants with bound tailed DNA amplified with MTHFR specific primers. Lanes 1-10 show: (1) tailed DNA bound to streptavidin beads; (2) ½ of supernatant from Lane 1 streptavidin beads; (3) streptavidin beads with ½ of supernatant from Lane 1; (4) ½ of supernatant from Lane 3 streptavidin beads; (5) streptavidin beads with ½ of supernatant from Lane 3; (6) ½ of supernatant from Lane 5 streptavidin beads; (7) streptavidin beads with ½ of supernatant from Lane 5; (8) ½ of supernatant from Lane 7 streptavidin beads; (9) DNA control; and (10) no template control.

Experiment 4: This experiment demonstrates bead binding of poly T/U tail. All samples were amplified with MTHFR specific primers for 25 cycles. FIG. 16 shows gel imaging of the PCR of streptavidin beads and supernatants. These results show that the DNA was bound to streptavidin Beads and able to be amplified under the standard PCR conditions. 10 pmol of 135-base single-stranded MTHFR Ultramer oligonucleotide (IDT) was tailed and added to 50 µl of Dynabeads M-280 streptavidin (10 mg/ml, 6×10^8 beads/ml). 1 mg of Dynabeads have a binding capacity of 10 ug of DNA or 200 pmol of oligonucleotides. In this experiment, the theoretical binding capacity was 10 pmol of oligonucleotide, which equates to 6×10^12 copies of duplexed dsDNA oligonucleotide. The experiment was repeated with 10 ng of DNA.

Figure 17:
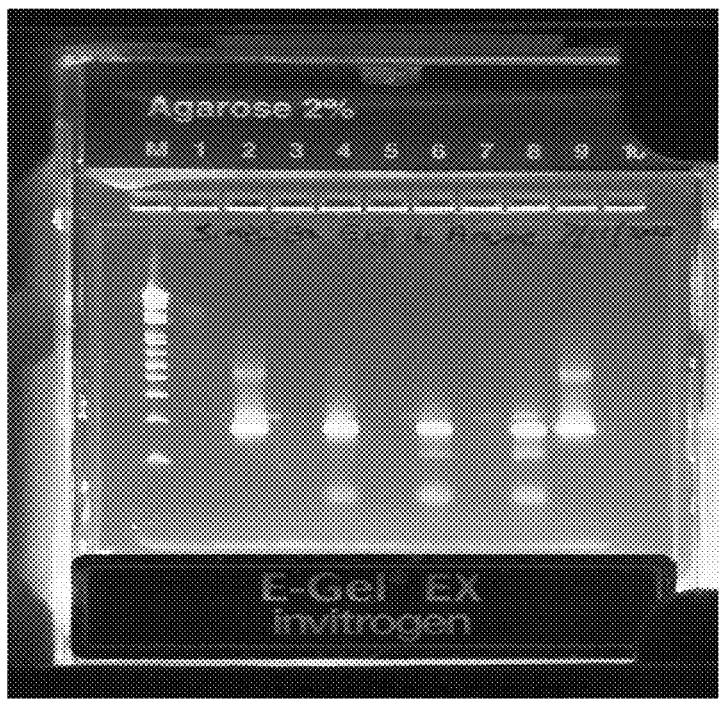
FIG. 17 is the gel image showing the control for non-specific binding by the amine modified DNA added to streptavidin beads. Lanes 1-10 show: (1) tailed DNA bound to streptavidin beads; (2) ½ of supernatant from Lane 1 streptavidin beads; (3) streptavidin beads with ½ of supernatant from Lane 1; (4) ½ of supernatant from Lane 3 streptavidin beads; (5) streptavidin beads with ½ of supernatant from Lane 3; (6) ½ of supernatant from Lane 5 streptavidin beads; (7) streptavidin beads with ½ of supernatant from Lane 5; (8) ½ of supernatant from Lane 7 streptavidin beads; (9) DNA control; and (10) no template control.

Experiment 5: This experiment is a control for non-specific binding, in which the amine modified DNA was added to streptavidin beads. As shown in FIG. 17, no amplification was observed in the wells containing beads, with amplification observed in all supernatant wells.

Experiment 6: This experiment demonstrates control DNA binding. Eight unique DNA samples and 1 oligo control were tailed and bound, and then subjected to qPCR. The qPCR was also performed using the beads bound with biotin-tailed DNA, azide-tailed DNA or DBCO-tailed DNA. The results showed an average of 7.7 cycle difference (range 5.2-13.1) between DNA bound to beads and DNA remaining in the supernatant from binding. This result suggests that over 99% of DNA was bound to the beads. Analysis of the beads bound with biotin-tailed DNA, azide-tailed DNA or DBCO-tailed DNA showed amplification on the beads stored at 4° C. for over 30 days. Amplification was also observed in the supernatant of these samples indicating possible degradation of beads or DNA.

Example 5: NGS Experiment: Plasma Tailing and Binding to Strepavidin Beads

HT29 DNA samples were run on a NextSeq 500 (Illumina, San Diego Calif.) to produce paired 75 bp reads. Those reads were analyzed using the Illumina BaseSpace cloud based analysis tool with the DNA Amplicon application (Illumina, San Diego Calif.). Both of the bound samples were tailed and bound via biotin-streptavidin affinity using beads. Beads containing bound HT29 DNA were added directly to the first PCR reaction with the HT29 Stock and HT29 fragment samples were DNA in solution without any additional manipulation and run as controls for the quality of data derived from the bound DNA samples. HT29 DNA was spiked into plasma, showing that TdT was active in plasma. An AmpliSeq panel interrogated 90 genomic regions. More specifically, a custom panel analyzing 90 genomics regions of interest was created using AmpliSeq for Illumina assay chemistry. This panel was validated in house using extracted and purified DNA. As shown in Table 2 below, bead bound DNA demonstrated improved uniformity of coverage and percentage of aligned reads compared to standard aqueous DNA samples. Table 2 shows various metrics commonly used for QC of NGS data. Each of these columns represent values used to determine the quality of the data produced by the sequencer and sample preparation methodologies. Pass Filter (PF) read are the total number of reads passing Illumina QC metrics. These reads have read lengths and error rates below an instrument defined threshold. % Q30 bases provides the percentage of bases that have less than 1 error per 10,000 bases. On target aligned Pass Filter (PF) reads are the total number of reads passing Illumina QC metrics that map to the region of the genome covered by the 90-region custom panel. SNV HET/HOM ratio and SNV Ts/Tv ratio are metrics designed to provide information on prevalence of heterozygous and homozygous mutations. In a diploid organism such as humans the expected ratio would be 2. Fragmented DNA (frag) in this experiment represents HT29 DNA fragmented to mimic the size of DNA expected to be found in plasma (typically ~150 bp). This fragmented DNA was then added to plasma samples to see if the reactions could be carried out in biological solutions. Negative control (Neg) had no DNA added to the assay. This was included because indexing barcodes have error rates and can be mis-assigned due to these errors. In this experiment, about 0.1% of the reads were assigned to the "Neg" sample. These were arbitrary and included only to show that the read counts in both the controls and beads were meaningful and not simply noise or errors.

TABLE 2

| | Sample | On-target aligned reads | % On-target PF reads | % Aligned reads | % Q30 bases | Amplicon mean coverage | Uniformity of coverage | SNV Het/Hom ratio | SNV Ts/Tv ratio |
|---|---|---|---|---|---|---|---|---|---|
| On Bead | HT29-Frag | 4,936,747 | 84.9 | 90.6 | 91.8 | 55,469 | 88.8 | 2.0 | 2.1 |
| | HT29-Frag-plasma | 6,923,178 | 85.9 | 91.4 | 92.3 | 77,789 | 87.6 | 2.0 | 2.1 |
| | HT29-Frag-no-tail | 3,214 | 24.7 | 26.3 | 63.9 | 36 | 27.0 | 0.0 | 1.0 |
| No Bead Control | HT29-Stock | 1,176,053 | 60.9 | 66.2 | 91.6 | 13,214 | 79.8 | 2.1 | 1.8 |
| | HT29-Frag-pure | 1,615,900 | 69.1 | 75.4 | 91.5 | 18,156 | 82.0 | 2.1 | 1.8 |
| | Neg | 1,530 | 3.7 | 6.2 | 43.1 | 17 | 19.1 | N/A | N/A |

This example demonstrates that both solution and plasma tailed and bound HT29 provides increased percentage of aligned reads and uniformity of coverage compared to stock and fragmented DNA.

Example 6: NGS Experiment: Use of Commercial Adapters

Figure 18:
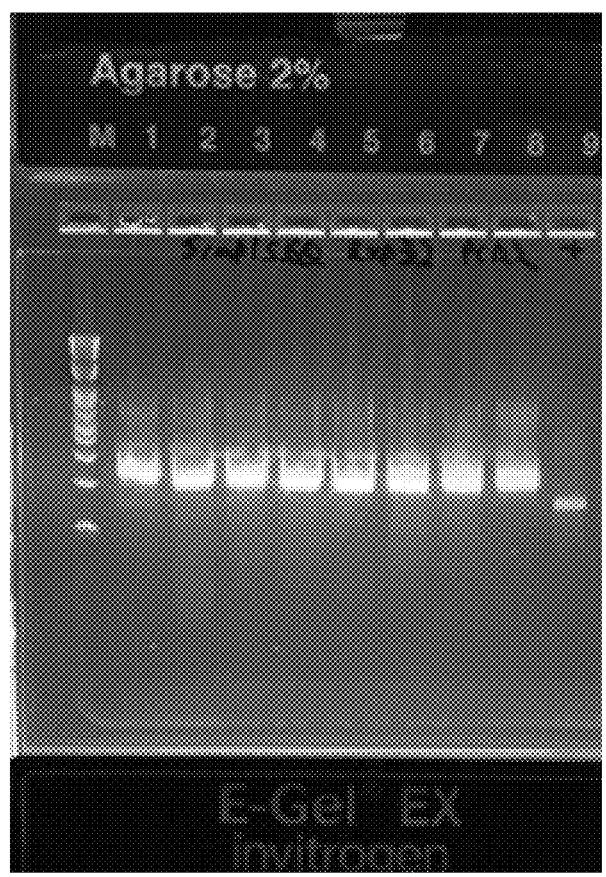
FIG. 18 is a gel image showing addition of Illumina adapters to MTHFR amplicons (lanes 1-8) compared to MTHFR amplicon (lane 9).

FIG. 18 is a gel image showing addition of Illumina adapters to MTHFR amplicons (lanes 1-8), and MTHFR amplicon without adaptor as a control (lane 9). Tailed bound DNA was amplified using MTHFR specific primers. The primers had 5' ends with sequence that overlapped with the Illumina adapters which served as priming sites for PCR addition of the Illumina indexes and full adapter sequence for addition to NGS flow cells.

MTHFR oligo library was prepared by addition of Illumina adapters using PCR primer with 3' complementary to the MTHFR tagged primer set.

Example 7: Use of Bead Bound DNA in Cancer Panel

Figure 19:
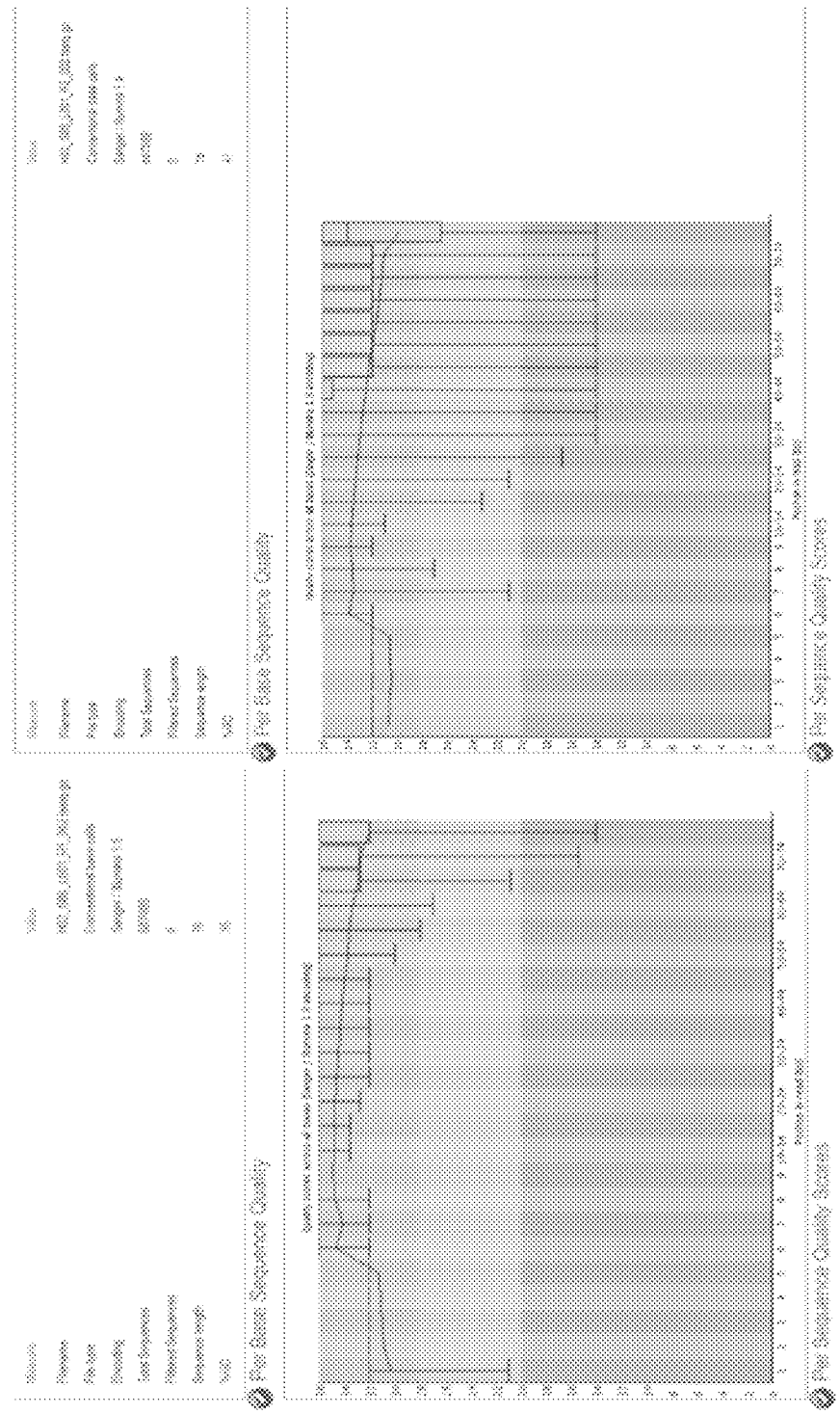
FIG. 19 illustrates the data for tagged primers. The FASTQC results showed proper incorporation of primer and extension on streptavidin bead bound DNA.
Figure 20A:
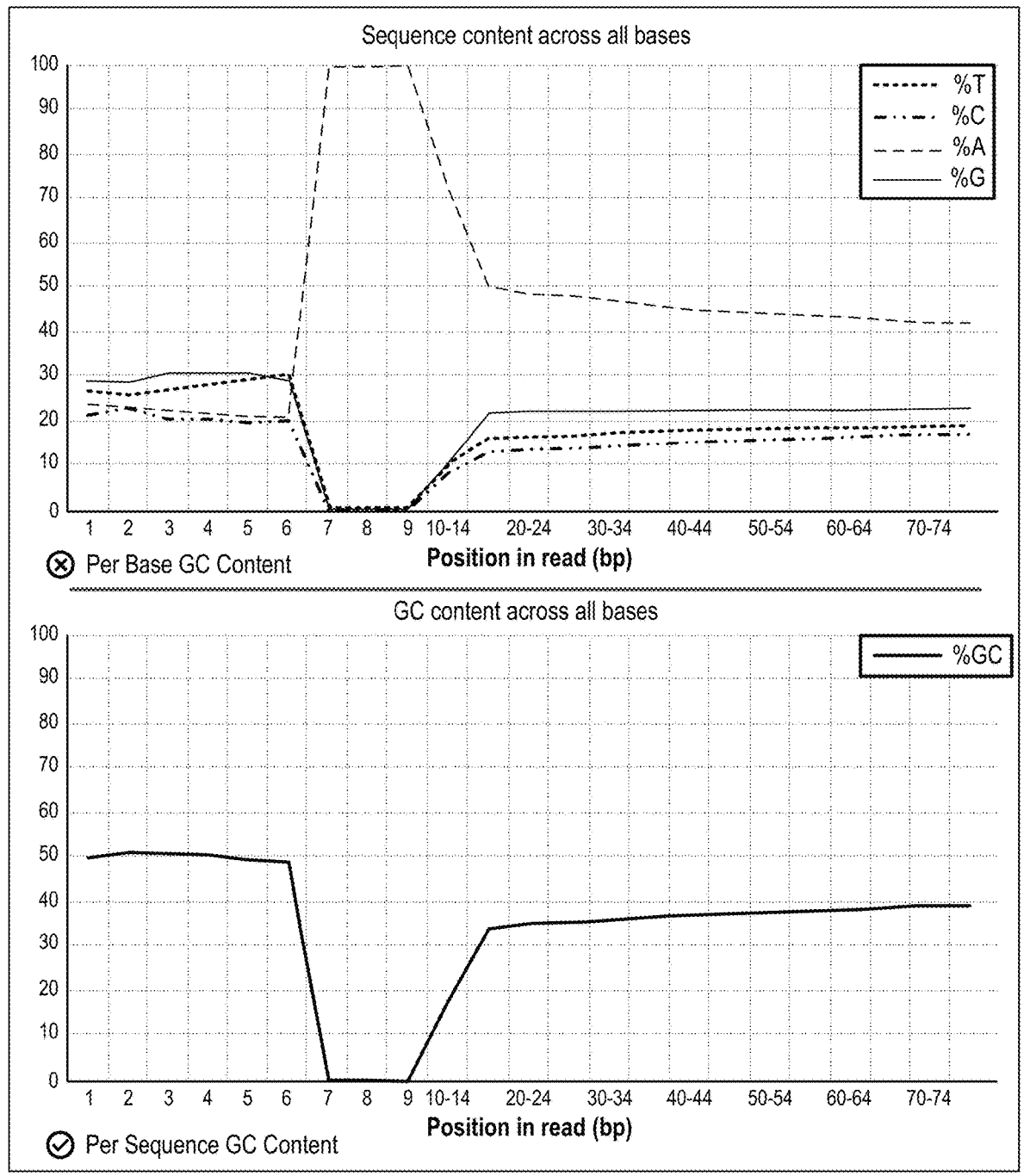
FIG. 20A shows high quality reads with full length sequence for both forward and reverse reads.
Figure 20B:
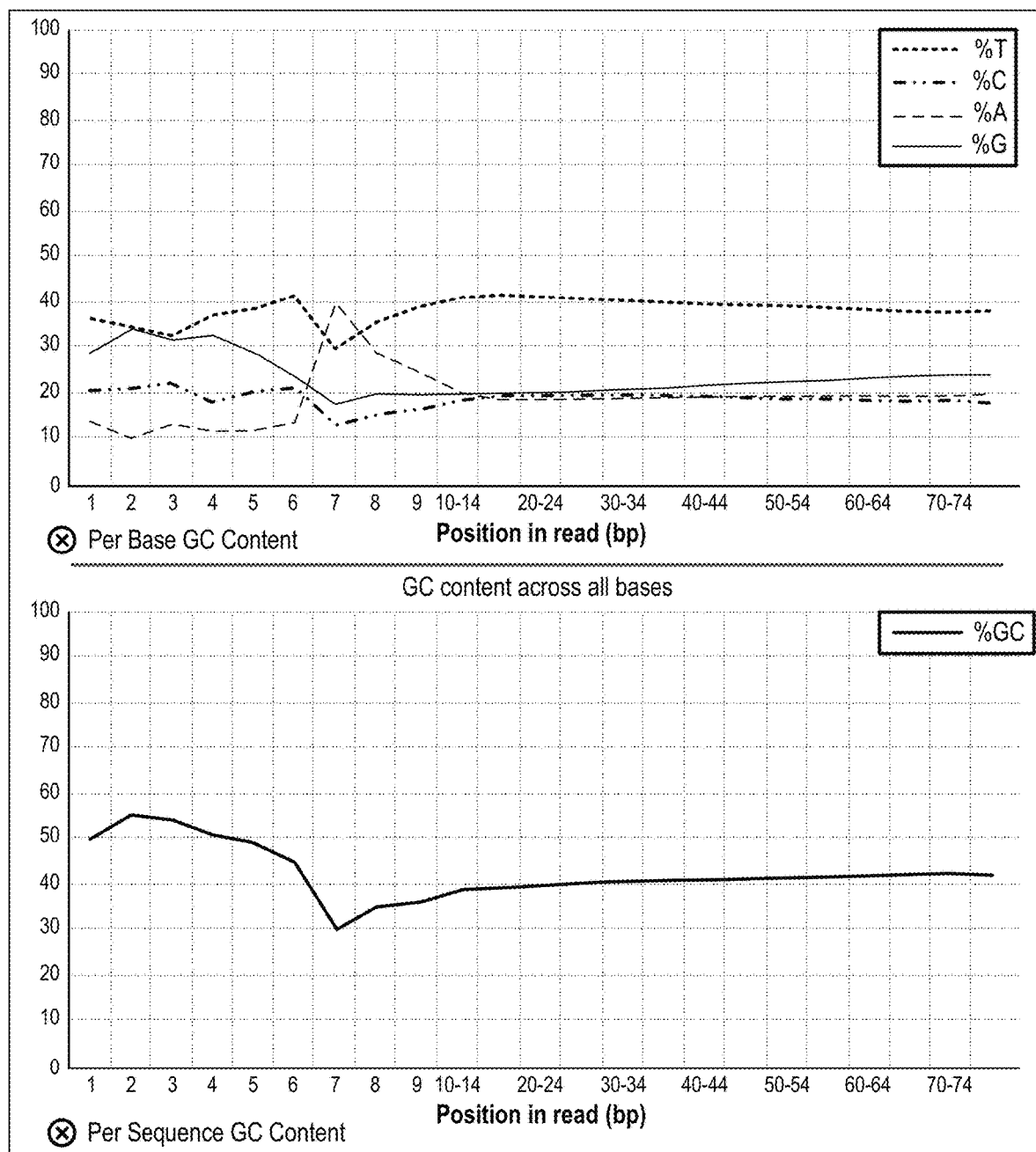
FIG. 20B shows that Read 2 using gene specific primer exhibits common base distribution, demonstrating that strand and directionality can be derived from the data.
Figure 20C:
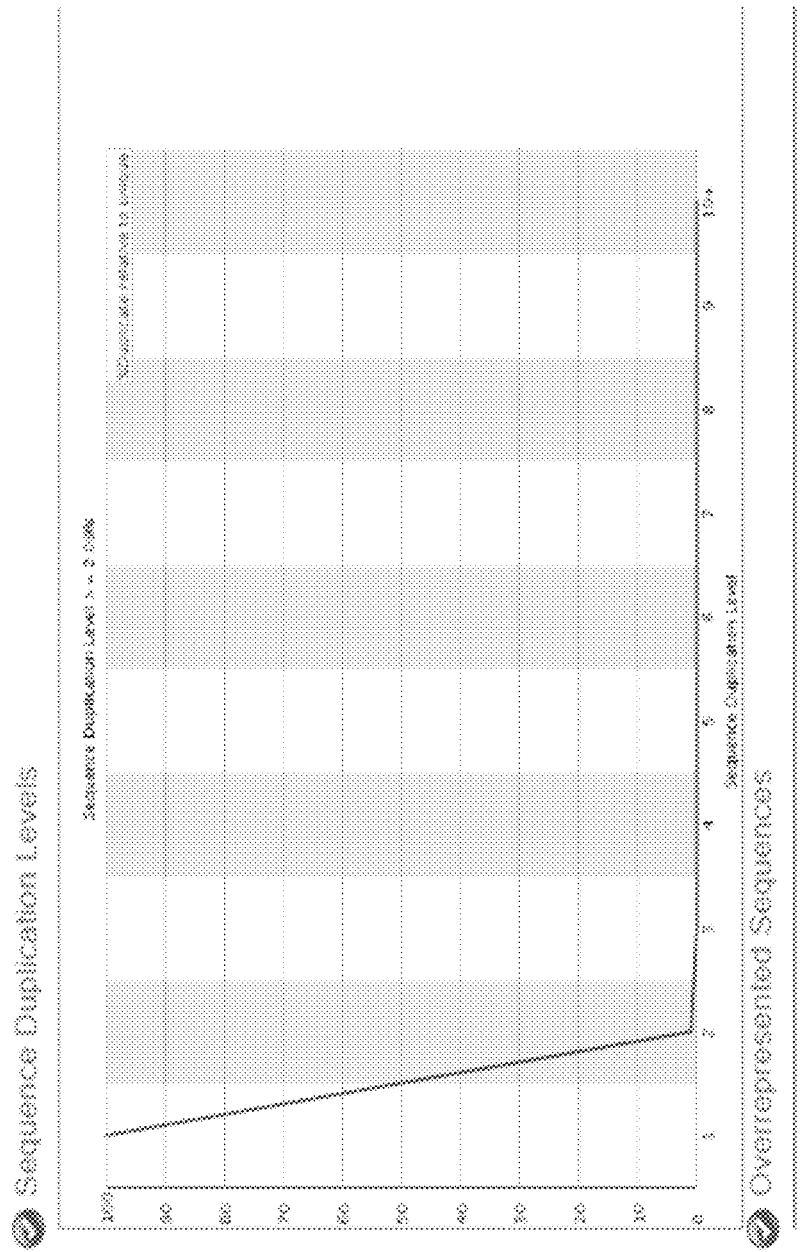
FIG. 20C shows low level of duplicate reads.

FIG. 19 illustrates FASTQC results showing proper incorporation of primer on streptavidin bead bound DNA. Primer included 5' Illumina tag, random hexamers then PolyA6 with a 3' terminal mixed base of (C, G, T). FIG. 20 demonstrates that strand and directionality information can be derived from sequence reads. Only low levels of duplicates were observed for about 2.8 million paired reads. This experiment used polyT tailed DNA bound to streptavidin beads via biotin-dUTP. A primer composed of a stubby adapter for Illumina primer addition, 6 random bases for unique molecular identification and 6 A bases and a mixture of C/G/T bases at the 3' end of the DNA primer. These 6 A bases would bind to the polyT tail of the streptavidin bound DNA at multiple locations. The mixed base (C/G/T) was added such that cDNA synthesis would begin at the first non T base in the bound DNA.

Example 8: Click Chemistry Binding

Figure 21:
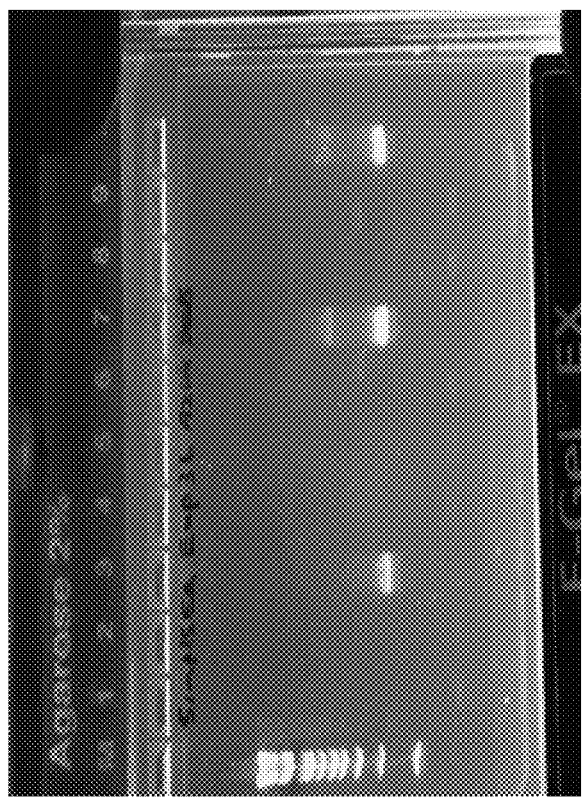
FIG. 21 is a gel image showing azide beads' specific binding to DBCO tailed products using terminal transferase (TdT) from different vendors. Lanes 1-10 include the following: (1) azide tailed DNA (Invitrogen TdT); (2) biotin tailed DNA (Invitrogen TdT); (3) DBCO tailed DNA (Invitrogen TdT); (4) untailed DNA; (5) azide tailed DNA (NEB TdT); (6) biotin tailed DNA (NEB TdT); (7) DBCO tailed DNA (NEB TdT); (8) untailed DNA; (9) azide bead control; and (10) PCR positive control.

FIG. 21 is a gel image showing that the azide beads were able to specifically bind to DBCO tailed products. Azide beads are specific for DBCO modification only, without binding of azide or biotin modified DNA.

In another experiment, 12 DNA samples were used to test click chemistry binding. The azide tailed DNA samples were bound to DBCO beads. PCR amplification of the DNA was successful on beads.

In another experiment, dUTPs modified with biotin, azide or DBCO were used for tailing and binding of oligos. dUTP modified with DBCO bound to azide beads demonstrated the best performance and no non-specific amplification was observed.

Example 9: Long Term Storage of DNA Bound to Beads

Figure 22:
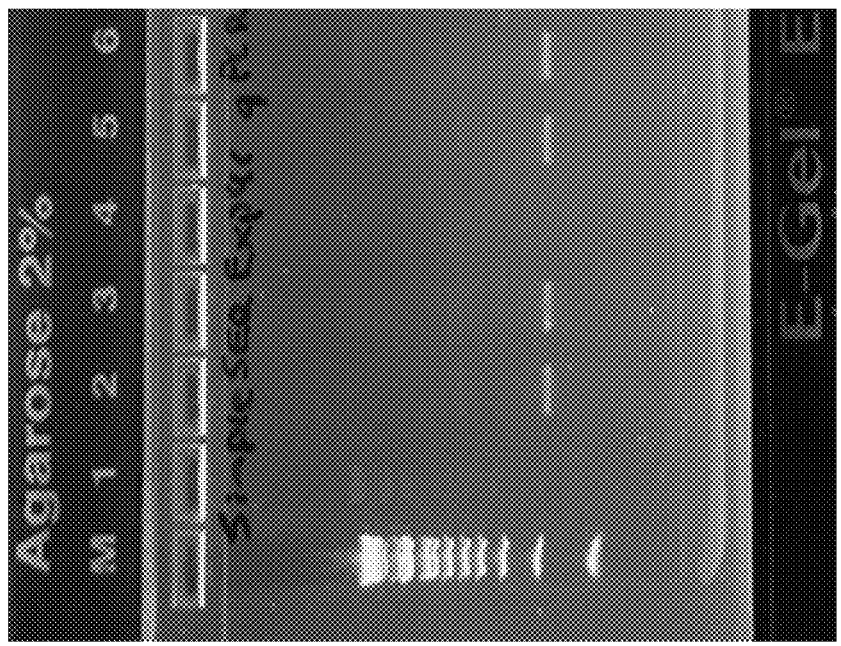
FIG. 22 is a gel image showing long term storage of the DNA bound to beads. Lanes 1-6 include the following: (1) azide bead SKBR3 supernatant 10 day time point (no DNA released from beads over 10 days); (2) azide beads bound with SKBR3 DNA; (3) azide bead supernatant from binding of tailed SKBR3 DNA; (4) azide bead HD778 supernatant 10 day time point (no DNA released from beads over 10 days); (5) azide beads bound with HD778 DNA; and (6) azide bead supernatant from binding of tailed HD778 DNA.

DBCO tailed DNA bound to Azide beads were stored at 4° C. for 10 days. qPCR comparing supernatant vs. beads showed a 7.7 average Ct difference from bound to supernatant. Ct values are the "Cycle Threshold" where the signal of amplified DNA in a given sample attains a fluorescent intensity above a background signal threshold. This is used to determine the relative quantity of DNA added to the qPCR reaction. Thus, a 208-fold (2^7.7) difference between bound DNA and supernatant demonstrates that 99.5% DNA remained bound to beads after 10-day storage. FIG. 22 shows the gel image.

Example 10: RNA Tailing and Binding

Universal Human Reference RNA (UHRR) and Twist synthetic nCoV2 RNA were used as input and tailed with DBCO modified dUTP, followed by binding to Azide beads. Eight conditions were tested and comparisons were made with biotin and DBCO dUTP tails. Invitrogen (acquired by ThermoFisher) SuperScript IV reverse transcriptase was used to create cDNA using random hexamer primers. This product was then treated with RNase H to release the cDNA. The Invitrogen and NEB enzymes were also compared. cDNA synthesis was carried out on beads using random hexamers. Eluted cDNA was used as input for qPCR. After magnetic binding the supernatant was removed and used as a source for qPCR. All reactions were run on an ABI QuantStudio 6 instrument. Table 3 below shows specific binding of RNA using multiple vendors for terminal transferase (Invitrogen and NEB).

TABLE 3

|  |  | RNAsep 1 | Virus 2 | RNAsep 3 | Virus 4 | RNAsep 5 | Virus 6 | RNAsep 7 | Virus 8 | RNAsep 9 | Virus 10 |
|---|---|---|---|---|---|---|---|---|---|---|---|
| Invitrogen Azide beads | A | Und | Und | 31.9 | 34.7 | 30.9 | 29.3 | Und | 30.8 | 29.9 | Und |
| NEB Azide | B | Und | Und | 34.7 | 35.6 | 32.8 | 30.5 | Und | 28.9 | 30.9 | Und |
| Invitrogen Azide beads | A | Azide beads | | UHRR + nCoV2 | | UHRR + nCoV2 | | nCoV2 | | UHRR | |
| NEB Azide | B | Azide Beads | | UHRR + nCoV2 | | UHRR + nCoV2 | | nCoV2 | | UHRR | |

|  |  | RNAsep 11 | Virus 12 | RNAsep 13 | Virus 14 | RNAsep 15 | Virus 16 | RNAsep 17 | Virus 18 |
|---|---|---|---|---|---|---|---|---|---|
| Invitrogen Azide beads | A | 33.1 | 30.5 | 30.1 | 28.1 | Und | 33.4 | 30.0 | Und |
| NEB Azide | B | 34.1 | 36.5 | 32.4 | 32.0 | Und | 29.0 | 31.6 | Und |
| Invitrogen Azide beads | A | UHRR + nCoV2 | | UHRR + nCoV2 | | nCoV2 | | UHRR | |
| NEB Azide | B | UHRR + nCoV2 | | UHRR + nCoV2 | | nCoV2 | | UHRR | |

This example demonstrates that each condition successfully detected human, viral or a combination of both human and viral RNA. DBCO-azide bound samples outperformed biotin-streptavidin beads by 2 Ct on average. Both Invitrogen and NEB enzymes showed roughly equivalent data for each condition in this experiment.

Example 11: On-Bead Assays

Experiment 1: On Bead Ampliseq. DNA from 4 unique cancer cell lines was tested for tailing, bead binding and on bead cDNA synthesis. The beads were used as input for Ampliseq assays with replicates for each condition totaling 60 samples run. The data shows similar on target aligned reads compared to stock DNA solutions extracted with Qiagen kit. Uniformity for all bead conditions averaged 79% compared to 69% for Qiagen extracted stock DNA. Similar variant call rates were observed with half of the mean coverage, evidencing that reduced sequencing costs can generate equivalent results.

TABLE 4

| Sample ID | Percent on-target aligned reads | Amplicon mean coverage | Uniformity of coverage (Pct > 0.2 * mean) | Call rate |
|---|---|---|---|---|
| Purified DNA | 96.2 | 21753 | 69.4 | 98.6 |
| Tailed Bound Beads Amine | 95.9 | 611 | 80.9 | 92.3 |
| Tailed Bound Beads SAV | 91.8 | 1042 | 74.7 | 91.8 |
| PolyA Primed Beads | 96.3 | 43879 | 79.6 | 98.3 |
| PolyA Primed cDNA SAV | 93.7 | 752 | 80.3 | 92.6 |
| PolyA Primed cDNA Amine | 90 | 458 | 78.9 | 89.3 |
| Specific Primed Beads | 95.4 | 27755 | 80.3 | 96.3 |
| Specific Primed cDNA Amine | 82.1 | 827 | 78.1 | 92.4 |
| Specific Primed cDNA SAV | 89 | 677 | 81.2 | 92.8 |

Experiment 2: On Bead Ampliseq. DNA samples from 4 cancer cell lines were tailed and bound in triplicate samples. Each was run on the AmpliSeq assay using the bead bound samples. The beads were washed 3 times and the AmpliSeq assay was repeated. A total of 3 AmpliSeq assays was run on each of the replicates using the same beads after washing. The first AmpliSeq replicate produced data equivalent to the stock DNA. Each successive round of AmpliSeq assays using the washed beads produced data but reduced on target rates and coverage uniformity. A total of 48 samples were tested in this experiment.

TABLE 5

| Sample ID | Percent aligned reads | Percent on-target aligned reads | Amplicon mean coverage | Uniformity of coverage | Call rate |
|---|---|---|---|---|---|
| DNA control average (4 samples) | 80.9 | 65.7 | 8240 | 64.0 | 91.2 |
| Carboxy Bead average (12 samples) | 85.8 | 65.9 | 1048 | 67.0 | 83.4 |
| SAV Bead REP1 average (12 samples) | 87.5 | 28.1 | 6449 | 60.6 | 88.9 |
| SAV Bead REP2 average (12 samples) | 89.5 | 83.0 | 2260 | 24.8 | 64.3 |
| SAV Bead REP3 average (12 samples) | 73.0 | 54.0 | 780 | 27.7 | 57.2 |

Experiment 3: On Bead Specific Primer cDNA Synthesis. A biotinylated oligo dT with i5 adapter sequence bound to streptavidin beads produced a cDNA product. The cDNA was eluted off the beads and successfully amplified by PCR. Three oligos were used with 2 gene specific primers for the cDNA synthesis.

Experiment 4: On Bead PCR. Both sense and antisense oligos were tailed, bound and primed using a polyA6 primer with a mixed base (C/G/T) 3' and 5' tag, along with gene specific primers. The cDNA products produced on bead were eluted and successfully amplified by PCR.

Example 12: DNA Isolation and Purification from Blood Using Collection Tubes with Different Preservatives Blood samples were collected in Streck and EDTA tubes. The tubes were centrifuged at 600×g for 10 minutes at room temperature. The plasma was removed in 0.5 ml aliquots and placed in 1.5 ml LoBind Eppendorf tubes. The samples were either run as individual samples or spiked with 20 ng of SKBR3 cell line DNA. Table 6 shows 3 independent replicates carried out using the PCR based AmpliSeq NGS assay, which was performed according to Illumina's protocol (www.illumina.com/products/by-brand/ampliseq.html). The bead solution was used as input.

TABLE 6

| | Amplicon mean coverage | Coverage Uniformity | On-target aligned reads (%) |
|---|---|---|---|
| Streck-Rep1 | 3747 | 73.0 | 97.7 |
| Streck-Rep2 | 9863 | 73.0 | 97.0 |
| Streck-Rep3 | 2283 | 82.0 | 95.5 |
| Streck + SKBR3-Rep1 | 16548 | 67.4 | 97.6 |
| Streck + SKBR3-Rep2 | 12292 | 75.3 | 95.7 |
| Streck + SKBR3-Rep3 | 8009 | 69.7 | 97.5 |
| EDTA-Rep1 | 3270 | 74.2 | 95.5 |
| EDTA-Rep2 | 8408 | 76.4 | 95.6 |
| EDTA-Rep3 | 10456 | 76.4 | 96.0 |
| EDTA + SKBR3-Rep1 | 11759 | 76.4 | 95.4 |
| EDTA + SKBR3-Rep2 | 6953 | 74.2 | 95.2 |
| EDTA + SKBR3-Rep3 | 3530 | 79.8 | 94.5 |
| SKBR3-Rep1 | 2197 | 67.4 | 95.2 |
| SKBR3-Rep2 | 5550 | 65.2 | 93.4 |
| SKBR3-Rep3 | 2338 | 66.3 | 90.4 |
| SKBR3-Control-Rep1 | 10416 | 58.4 | 95.1 |
| SKBR3-Control-Rep2 | 11047 | 61.8 | 95.4 |
| SKBR3-Control-Rep3 | 13425 | 59.6 | 95.7 |

The data demonstrates consistent on-target aligned reads and improved uniformity compared to the SKBR3 control replicates run as standard DNA in solution.

Example 13: Effects of Poly a Primer Length on cDNA Synthesis

This example shows that a polyA primer having a size of either 6 nt or 20 nt can work for cDNA synthesis. Oligonucleotide primers were added at 1 pmol/reaction with 20 ng of biotin tailed oligonucleotide bound to streptavidin beads at a volume of 12 µl. This mixture was heated to 95° C. for 1 minute and slowly cooled down to 4° C. in Veriti Thermocycler under standard ramp speed conditions. After 2 minutes at 4° C., 18 µl of reaction mixture including 3 µl NEB Buffer 2, 0.5 µl of 10 mM dNTP mix, 1.5 µl Klenow Exo, and 13 µl of water was added. The samples were incubated at 16° C. for 30 minutes. Upon completion of the cDNA reaction, 2 µl of the bead reaction mixture was added to 1 µl of specific primer for MTHFR gene cDNA product and either i5 or i7 indexing adapter primer in 16 µl of reaction mixture including 4 µl of 5× Hemo KlenTaq buffer, 0.5 µl of 10 mM dNTP mix, 1 µl of IDT for Illumina primer set (used to add the sequence required for binding to the instrument flow cell and producing sequencing results), 1 µl of Hemo KlenTaq enzyme (25 U/µl), and 9.5 µl of water.

Figure 23:
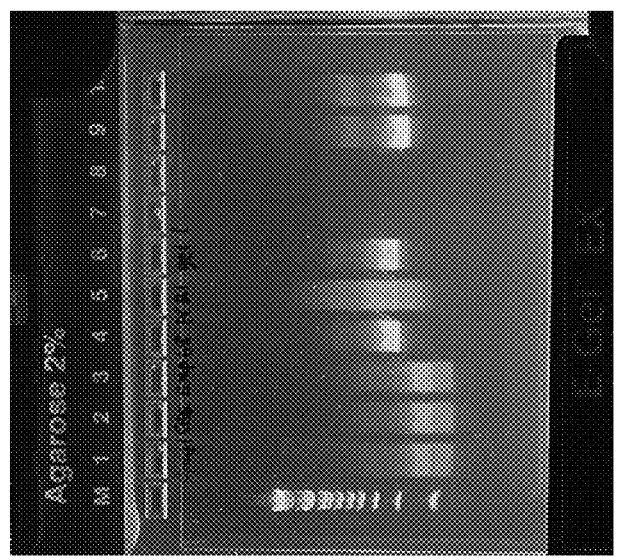
FIG. 23 is a gel image showing that only the matching primer sets produced bands of correct size (see lanes 4 and 6). Lanes 1-10 correspond to Samples 1-10 disclosed in Example 14.

This experiment was performed to demonstrate that the PolyA6B primer used for cDNA synthesis produced the correct product only when primer matched with MTHFR gene specific primer was used, as shown in FIG. 23.

Table 7 shows the samples and cDNA primers and PCR primers used in this experiment.

TABLE 7

| Sample No. | Sample ID | cDNA Primer | PCR Primer 1 | PCR Primer 2 |
|---|---|---|---|---|
| 1 | MTHFR RC PolyT | PolyA6 SP1 | IDT rhAmp Index primer i5 A1 | MTHFR R3 |

TABLE 7-continued

| Sample No. | Sample ID | cDNA Primer | PCR Primer 1 | PCR Primer 2 |
|---|---|---|---|---|
| 2 | MTHFR RC PolyT | PolyA6 SP2 | IDT rhAmp Index primer i5 A1 | MTHFR R3 |
| 3 | MTHFR RC PolyT | PolyA12 i5 | IDT rhAmp Index primer i5 A1 | MTHFR R3 |
| 4 | MTHFR RC PolyT | PolyA6 SP1 | IDT rhAmp Index primer i7 A1 | MTHFR R3 |
| 5 | MTHFR RC PolyT | PolyA6 SP2 | IDT rhAmp Index primer i7 A1 | MTHFR R3 |
| 6 | MTHFR RC PolyT | PolyA12 i5 | IDT rhAmp Index primer i7 A1 | MTHFR R3 |
| 7 | MTHFR RC PolyT | PolyA6 SP1 | PolyA6 SP1 | MTHFR R3 |
| 8 | MTHFR RC PolyT | PolyA6 SP2 | PolyA6 SP2 | MTHFR R3 |
| 9 | MTHFR RC PolyT | | MTHFR R2 | MTHFR R3 |
| 10 | hgDNA | | MTHFR R2 | MTHFR R3 |

Example 14: Long Term Storage and Stability of Tailed DNA Bound to Beads

This example shows whole genome cDNA synthesis replicates run on the same bead sample over the time course of 3 weeks. The SKBR3 cell line DNA was spiked into human plasma sample collected in Streck and EDTA tubes. The tailing reaction was carried out at room temperature overnight directly in plasma. Replicates of the bound DNA was taken after 7 days and 21 days. A total of 4 replicates were taken from the same set of beads stored at 4° C. Using the cDNA synthesis process according to Example 3, ligation with the new adapters was performed for each replicate proving that unique cDNA was synthesized and that the 5' end of the bound DNA had a ligated adapter. After each cDNA synthesis and ligation reaction, the beads were washed 3 times with 10 mM Tris HCl pH 8, and resuspended in 10 mM Tris HCl buffer.

Figure 25:
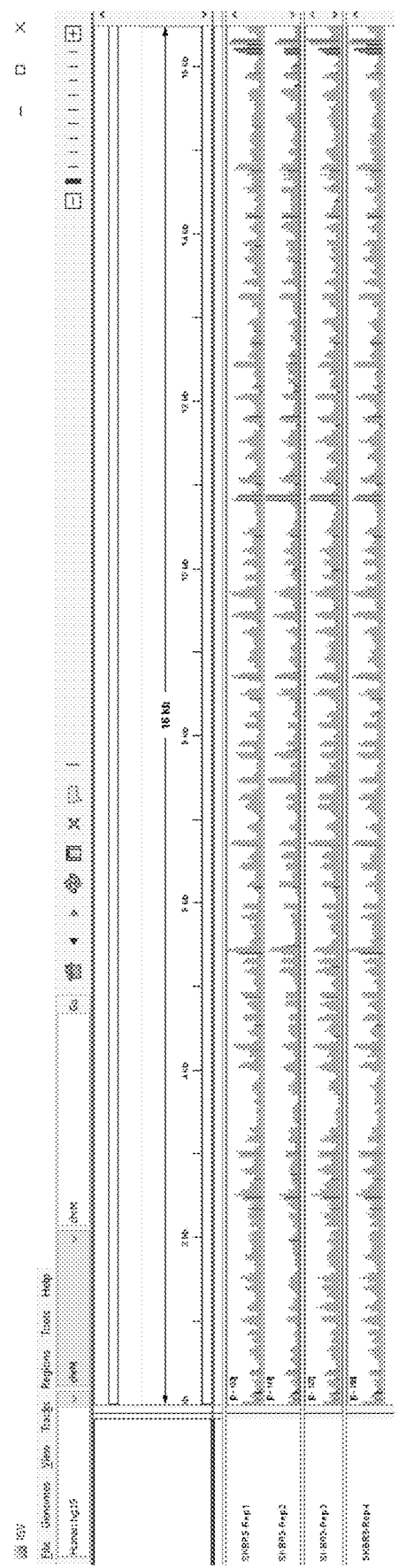
FIG. 25 is an Integrative Genomics Viewer (IGV) image showing the 4 replicates of SKBR3 DNA bound to streptavidin beads.

FIG. 25 is an Integrative Genomics Viewer (IGV) image showing the 4 replicates of SKBR3 DNA bound to streptavidin beads. The coverage of mitochondrial genome was reasonably uniform as shown in FIG. 25. The IGV plots also show that each replicate had high degree of coverage uniformity when compared to each other.

Example 15: Bound PolyA RT cDNA Synthesis

Targeted or randomly primed DNA or RNA assays are performed using the follow reaction conditions, as illustrated in FIG. 26. An oligonucleotide primer is synthesized with 5' biotin, containing a polyU linker followed by an i5 adapter sequence and a terminal PolyA 3' tail. This oligonucleotide is attached to a streptavidin bead and serves as a primer for hybridization and cDNA synthesis according to magnetic beads vendor's protocol (www.neb.com/protocols/0001/01/01/cdna-synthesis-on-oligo-dt25-magnetic-beads-s1419). The addition of an adapter provides an opportunity to create a simple cDNA library ready for analysis with either random or specific primed second strand primer that contains the i7 adapter sequence to be used in Illumina NGS instrumentation.

Example 16: Whole Genome Sequencing of DNA Sample

Figure 28:
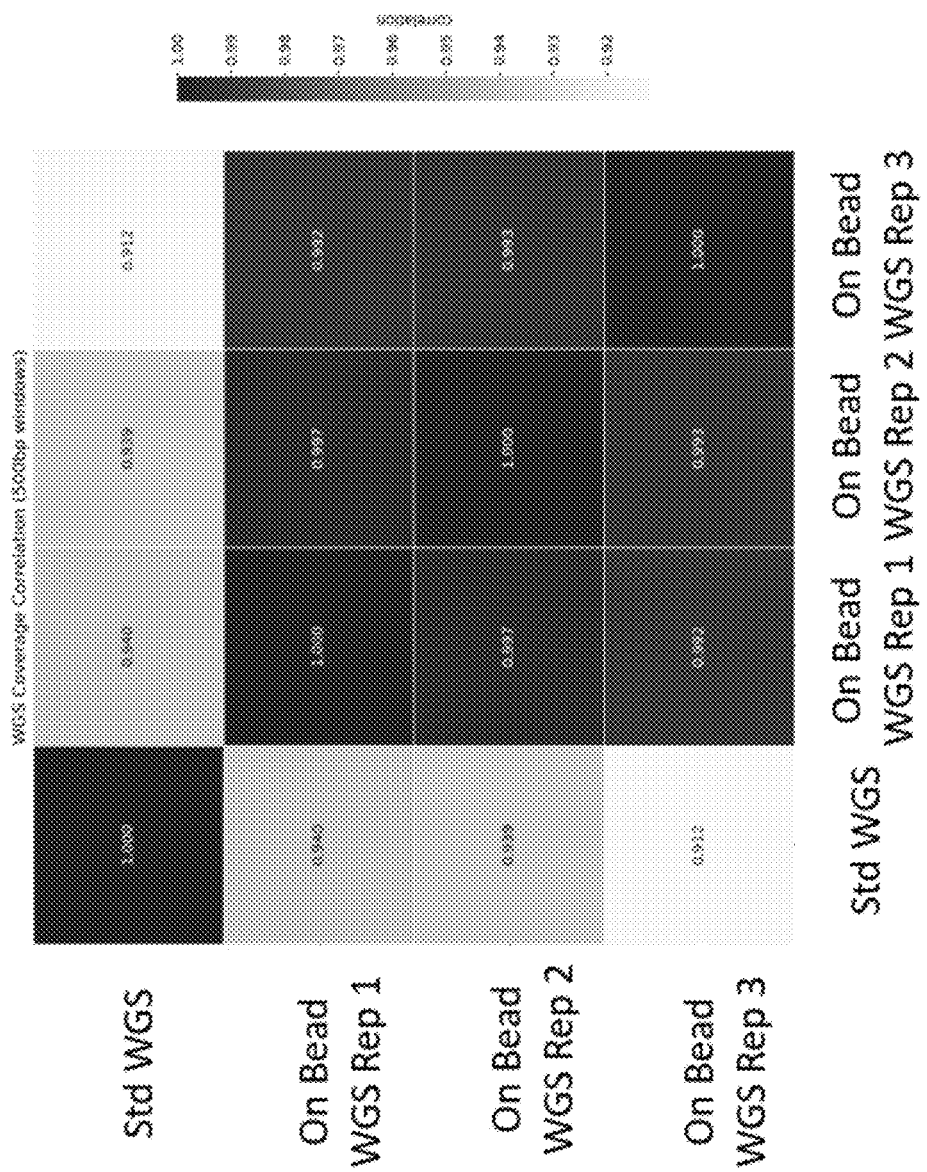
FIG. 28 shows DNA whole genome sequencing correlation. A single purified DNA sample was used to assess the ability to create copies of tailed and bound DNA.

FIG. 28 shows high level of correlation for whole genome sequencing replicates. Two hundred ng of DNA sample was processed using Kapa Biosystems WGS Hyper Plus prep kit (sequencing.roche.com/en/products-solutions/products/sample-preparation/dna-reagents/library-preparation/kapa-hyperplus.html). The DNA sample was enzymatically fragmented, end repaired, and tailed and with Illumina adapters ligated. After purification of the ligated product, half of the sample was used for standard Kapa WGS PCR for 5 cycles. The other half of the sample was tailed with dUTP and biotinylated ddUTP by incubating at 37° C. for 60 minutes and bound to streptavidin beads for 30 minutes at room temperature. The streptavidin beads were washed 3 times with 10 mM Tris HCl pH 8.0. A unique set of IDT indexing adapters were added to the beads for a 5 cycle PCR reaction. The PCR supernatant was removed and the beads were washed 3 times with 10 mM Tris HCl pH 8.0. The PCR process was repeated using a new set of unique index primers. This process was repeated for all 3 replicates. All 3 PCR replicates and the standard Kapa PCR sample were purified using AMPure XP beads at a 1.5× volume:volume ratio. Each sample was quantitated and added to a single library for NGS sequencing. FIG. 28 shows the concordance for each on bead PCR replicate compared to the standard Kapa PCR protocol. The results show that the DNA was tailed, bound to beads and able to have multiple copies made that have a near perfect correlation. The standard whole genome sequencing sample and all 3 replicates had nearly identical quality metric and high correlation as shown in FIG. 28 and Table 8 below. The rightmost column of Table 8 shows the percentage of the genome that has at least 1 read covering it. A coverage similar to the standard WGS preparation was observed.

TABLE 8

| Sample Name | % GC | % Aligned | Insert Size | ≥1X |
|---|---|---|---|---|
| STD WGS | 41% | 100% | 320 bp | 92.00% |
| On Bead-Rep1 | 41% | 100% | 300 bp | 91.00% |
| On Bead-Rep2 | 41% | 100% | 278 bp | 91.00% |
| On Bead-Rep3 | 41% | 100% | 278 bp | 91.00% |

Example 17: Whole Genome Sequencing of Plasma Sample

Whole genome sequencing was performed on plasma samples collected from a subject using a plasma sample spiked with DNA as a control. The first sample was a plasma sample spiked with 50 ng of DNA before tailing. This sample served as a control to confirm that the assay was able to work in plasma with a known amount of DNA. The second sample contained plasma only without exogenous DNA spiking. The samples were whole genome sequenced in replicates, and the results are shown in Table 9 below. The 96% alignment could be due to other types of DNA being present in the plasma and not only human DNA was present.

TABLE 9

| Sample Name | % Aligned | ≥1X |
|---|---|---|
| Plasma + DNA spike Rep 1 | 96% | 87.0% |
| Plasma + DNA spike Rep 1 | 96% | 90.0% |
| Plasma (no spiking) Rep 1 | 96% | 82.0% |
| Plasma (no spiking) Rep 2 | 84% | 49.0% |

REFERENCES

The references, patents and published patent applications listed below, and all references cited in the specification above are hereby incorporated by reference in their entireties, as if fully set forth herein.

1. Butt A N et al., Overview of circulating nucleic acids in plasma/serum, Ann N. Y. Acad. Sci. 1137: 236-242 (2008).
2. Casadio V. et al., Urine cell-free DNA integrity as a marker for early prostate cancer diagnosis: a pilot study, Biomed Research International 2013: 270457 (2013).
3. Kemp B M et al., How much DNA is lost? Measuring DNA loss of short-tandem-repeat length fragments targeted by the PowerPlex 16® system using the Qiagen MinElute Purification Kit, Hum. Biol. 86: 313-329 (2014).
4. Motea et al., Terminal deoxynucleotidyl transferase: The story of a misguided DNA polymerase, Biochimica et Biophysica Acta (BBA)—Proteins and Proteomics 1804: 1151-1166 (2010).
5. Sasaki R. et al., TdT activity in bone-marrow serum in patients with leukemia, The New England J. of Medicine 304: 1108 (1981).
6. Rashid, The strategies of DNA immobilization and hybridization detection mechanism in the construction of electrochemical DNA sensor: a review, Sensing and Bio-Sensing Research 16: 19-31 (2017).
7. Kosiova et al., Synthesis of coumarin or ferrocene labeled nucleosides via Staudinger ligation, Beilstein J. Org. Chem. 2, No. 23. doi:10.1186/1860-5397-2-23 (2006).

The invention claimed is:

1. A method of isolating nucleic acid fragments, comprising:
contacting a biological sample containing nucleic acid fragments with a reaction mix comprising a template-independent DNA or RNA polymerase, and one or more NTPs, dNTPs or ddNTPs, wherein at least a fraction of the one or more NTPs, dNTPs or ddNTPs are modified by an affinity tag, to obtain tagged nucleic acid fragments;
binding the tagged nucleic acid fragments to a surface of a solid support; and
washing the solid support to obtain the bound nucleic acid fragments isolated from the biological sample,
wherein the biological sample is selected from the group consisting of blood, plasma, serum, urine, saliva, exosome, a lysed formalin-fixed, paraffin-embedded (FFPE) tissue sample, and cells.

2. The method of claim 1, wherein the nucleic acid fragments are DNA fragments, RNA fragments, or a mixture of both.

3. The method of claim 1, wherein the nucleic acid fragments are double-stranded, single-stranded, or a mixture of both.

4. The method of claim 3, wherein the double-stranded nucleic acid fragments are denatured to single-stranded nucleic acid fragments before or after contacting the biological sample with the reaction mix.

5. The method of claim 1, wherein the template-independent DNA or RNA polymerase is terminal transferase (TdT).

6. The method of claim 1, wherein the affinity tag is biotin, and the surface of the solid support is coated with avidin, streptavidin, or neutravidin.

7. The method of claim 1, wherein the reaction mix comprises biotinylated dUTP or biotinylated ddUTP.

8. The method of claim 1, wherein a polymeric tail comprising the unmodified and modified NTPs, dNTPs or ddNTPs is attached to a 3' end of the nucleic acid fragments.

9. The method of claim 1, further comprising removing the bound isolated nucleic acid fragments from the surface of the solid support by enzyme digestion.

10. The method of claim 1, wherein the solid support is a bead, a plate, or a column.

11. A method of isolating nucleic acid fragments comprising:
combining a blood or plasma sample containing nucleic acid fragments with a reaction mix comprising a template-independent DNA or RNA polymerase, and one or more NTPs, dNTPs or ddNTPs, wherein at least a fraction of the one or more NTPs, dNTPs or ddNTPs are modified by a biotin affinity tag, to obtain nucleic acid fragments having a biotin tagged polymeric tail;
binding the biotin tagged nucleic acid fragments to a solid support surface coated with avidin, streptavidin, or neutravidin; and
washing the solid support to isolate the bound nucleic acid fragments from the blood or plasma sample.

12. The method of claim 11, wherein the nucleic acid fragments are DNA or RNA fragments.

13. The method of claim 11, wherein the nucleic acid fragments are double-stranded or single-stranded fragments.

14. The method of claim 11, wherein the double-stranded nucleic acid fragments are denatured to single-stranded nucleic acid fragments before or after contacting the blood or plasma sample with the reaction mix.

15. The method of claim 11, wherein the template-independent DNA or RNA polymerase is terminal transferase (TdT).

16. The method of claim 11, wherein the reaction mix comprises biotinylated dUTP or biotinylated ddUTP.

17. The method of claim 11, wherein the polymeric tail is attached to a 3' end of the nucleic acid fragments.

18. The method of claim 11, wherein the solid support is a bead, a plate, or a column.

19. A method of isolating DNA fragments comprising:
combining a blood or plasma sample containing DNA fragments with a reaction mix comprising a template-independent DNA polymerase, and one or more NTPs, dNTPs or ddNTPs, wherein at least a fraction of the NTPs, dNTPs or ddNTPs are modified by a biotin affinity tag, to obtain nucleic acid fragments having a biotin tagged polymeric tail;
binding the biotin tagged DNA fragments to a solid support surface coated with avidin, streptavidin, or neutravidin; and
washing the solid support to isolate the bound DNA fragments from the blood or plasma sample.

20. The method of claim 19, wherein the DNA fragments are double-stranded or single-stranded fragments.

21. The method of claim 19, wherein the double-stranded DNA fragments are denatured to single-stranded DNA fragments before or after contacting the blood or plasma sample with the reaction mix.

22. The method of claim 19, wherein the template-independent DNA polymerase is terminal transferase (TdT).

23. The method of claim 19, wherein the reaction mix comprises biotinylated dUTP or biotinylated ddUTP.

24. The method of claim 19, wherein the polymeric tail is attached to a 3' end of the DNA fragments.

25. The method of claim 19, further comprising removing the bound isolated nucleic acid from the surface of the solid support by enzyme digestion.

26. The method of claim 19, wherein the solid support is a bead, a plate, or a column.

27. A method of isolating DNA fragments comprising:
denaturing double stranded DNA fragments in a blood or plasma sample into single stranded DNA fragments having a 5' end and a 3' end;
combining the blood or plasma sample containing DNA fragments with a reaction mix comprising a terminal transferase (TdT), and one or more NTPs, dNTPs or ddNTPs, wherein at least a fraction of the NTPs, dNTPs or ddNTPs are modified by a biotin affinity tag, to obtain DNA fragments having a biotin tagged polymeric tail at the 3' end;
binding the biotin tagged DNA fragments to a solid support surface coated with avidin, streptavidin, or neutravidin; and
washing the solid support to isolate the bound DNA fragments from the blood or plasma sample.

28. The method of claim 27, wherein the reaction mix comprises biotinylated dUTP or biotinylated ddUTP.

29. The method of claim 27, wherein the solid support is a bead, a plate, or a column.

\* \* \* \* \*

UNITED STATES PATENT AND TRADEMARK OFFICE
CERTIFICATE OF CORRECTION

| | |
|---|---|
| PATENT NO. | : 11,268,087 B2 |
| APPLICATION NO. | : 17/331532 |
| DATED | : March 8, 2022 |
| INVENTOR(S) | : Brandon Michael Young |

It is certified that error appears in the above-identified patent and that said Letters Patent is hereby corrected as shown below:

In the Claims

In Column 31, Line 22, Claim 21, delete "claim 19" and insert --claim 20--, therefor.

Signed and Sealed this
Fourteenth Day of February, 2023

Katherine Kelly Vidal
*Director of the United States Patent and Trademark Office*